US012033057B2

(12) United States Patent
Sherman et al.

(10) Patent No.: US 12,033,057 B2
(45) Date of Patent: *Jul. 9, 2024

(54) SYSTEM FOR CLASSIFYING THE USAGE OF A HANDHELD CONSUMER DEVICE

(71) Applicant: Braun GmbH, Kronberg (DE)

(72) Inventors: Faiz Feisal Sherman, Mason, OH (US); Xiaole Mao, Mason, OH (US)

(73) Assignee: Braun GmbH, Kronberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/215,248

(22) Filed: Jun. 28, 2023

(65) Prior Publication Data

US 2023/0342423 A1 Oct. 26, 2023

Related U.S. Application Data

(63) Continuation of application No. 16/276,947, filed on Feb. 15, 2019, now Pat. No. 11,755,686.

(30) Foreign Application Priority Data

Feb. 19, 2018 (EP) ..................................... 18157358
Feb. 19, 2018 (EP) ..................................... 18157362

(51) Int. Cl.
*G06N 3/044* (2023.01)
*A46B 15/00* (2006.01)
(Continued)

(52) U.S. Cl.
CPC ......... *G06N 3/044* (2023.01); *A46B 15/0073* (2013.01); *A61C 17/22* (2013.01);
(Continued)

(58) Field of Classification Search
CPC ...... G06F 18/213; G06F 16/285; G06F 18/00; G06F 2218/16; A46B 15/0073;
(Continued)

(56) References Cited

U.S. PATENT DOCUMENTS 7,835,999 B2 11/2010 Block
7,877,338 B2 1/2011 Tani
(Continued)

FOREIGN PATENT DOCUMENTS

CN 101367015 A 2/2009
CN 102265242 A 11/2011
(Continued)

OTHER PUBLICATIONS

Alex Graves, Abdel-rahman Mohamed and Geoffrey Hinton; "Speech Recognition With Deep Recurrent Neural Networks"; Department of Computer Science, University of Toronto; Mar. 22, 2013, 05 Pages.
(Continued)

*Primary Examiner* — Quan Zhen Wang
*Assistant Examiner* — Rajsheed O Black-Childress
(74) *Attorney, Agent, or Firm* — Gregory S. Darley-Emerson

(57) ABSTRACT

A system for classifying the usage of a handheld consumer device having a sensor and an analyzer. The sensor determines usage data at successive time instants and provides a temporally successive sequence of usage data during a usage session. The analyzer classifies the usage of the device with respect to at least one set usage classes and assembles a temporally successive sequence of input tuples of usage data relating to a predetermined time period of the usage session, each of the input tuples having at least one element representing the usage data at the respective time instant and for inputting the sequence of input tuples into at least one artificial neural network arranged to output at least one output tuple comprising a number of elements in accordance with the number of usage classes, each element of the output tuple representing a prediction value that the usage of the
(Continued)

consumer device at the given time instant relates to a respective usage class.

22 Claims, 9 Drawing Sheets

(51) Int. Cl.

| | | |
|---|---|---|
| *A61C 17/16* | (2006.01) | |
| *A61C 17/22* | (2006.01) | |
| *A61C 17/26* | (2006.01) | |
| *A61C 17/34* | (2006.01) | |
| *B26B 21/40* | (2006.01) | |
| *G06F 16/28* | (2019.01) | |
| *G06N 3/08* | (2023.01) | |
| *G06V 40/20* | (2022.01) | |
| *G08B 21/18* | (2006.01) | |

(52) U.S. Cl.
CPC ............ *A61C 17/221* (2013.01); *A61C 17/26* (2013.01); *G06F 16/285* (2019.01); *G06N 3/08* (2013.01); *G06V 40/20* (2022.01); *G08B 21/18* (2013.01); *A46B 15/0002* (2013.01); *A46B 15/0036* (2013.01); *A46B 15/0038* (2013.01); *A46B 15/004* (2013.01); *A46B 15/0071* (2013.01); *A46B 2200/1066* (2013.01); *A61B 2562/0219* (2013.01); *A61B 2562/0247* (2013.01); *A61B 2562/0252* (2013.01); *A61C 17/16* (2013.01); *A61C 17/3409* (2013.01); *B26B 21/4056* (2013.01); *B26B 21/4081* (2013.01); *G06F 2218/16* (2023.01)

(58) Field of Classification Search
CPC ............ A46B 15/0002; A46B 15/0036; A46B 15/0038; A46B 15/004; A46B 15/0071; A46B 2200/1066; A61C 17/22; A61C 17/221; A61C 17/26; A61C 17/16; A61C 17/3409; G06N 3/044; G06N 3/08; G06V 40/20; G08B 21/18; A61B 2562/0219; A61B 2562/0247; A61B 2562/0252; B26B 21/4056; B26B 21/4081
See application file for complete search history.

(56) References Cited

U.S. PATENT DOCUMENTS

| | | |
|---|---|---|
| 8,175,840 B2 | 5/2012 | Hwang et al. |
| 8,251,821 B1 | 8/2012 | Yen et al. |
| 8,554,707 B2 | 10/2013 | Schäfer |
| 9,144,476 B2 | 9/2015 | Iwahori |
| 9,263,036 B1 | 2/2016 | Graves |
| 9,292,102 B2 | 3/2016 | Nasiri et al. |
| 9,646,244 B2 | 5/2017 | Corrado |
| 9,820,233 B2 | 11/2017 | Pakzad et al. |
| 2003/0036835 A1 | 2/2003 | Breed et al. |
| 2005/0219213 A1 | 10/2005 | Cho et al. |
| 2008/0077326 A1 | 3/2008 | Funk et al. |
| 2008/0102953 A1 | 5/2008 | Schultz |
| 2008/0174550 A1 | 7/2008 | Laurila et al. |
| 2009/0092955 A1 | 4/2009 | Hwang |
| 2010/0145654 A1 | 6/2010 | Hwang |
| 2011/0010875 A1 | 1/2011 | Iwahori et al. |
| 2011/0060706 A1 | 3/2011 | Suzuki |
| 2014/0065588 A1 | 3/2014 | Jacobson et al. |
| 2014/0349256 A1 | 11/2014 | Connor |
| 2015/0109202 A1 | 4/2015 | Ataee et al. |
| 2015/0189008 A1 | 7/2015 | Krkkinen et al. |
| 2015/0316383 A1 | 11/2015 | Donikian |
| 2016/0073886 A1 | 3/2016 | Carniato |
| 2016/0091308 A1 | 3/2016 | Oliaei |
| 2016/0091965 A1 | 3/2016 | Wang |
| 2016/0143718 A1 | 5/2016 | Serval |
| 2016/0235357 A1 | 8/2016 | Ohmer |
| 2017/0069083 A1* | 3/2017 | Vetter .................. A61B 5/1128 |
| 2017/0173262 A1 | 6/2017 | Veltz |
| 2017/0176213 A1 | 6/2017 | Eriksson |
| 2017/0281054 A1 | 10/2017 | Stever et al. |
| 2017/0318954 A1 | 11/2017 | Nishiura et al. |
| 2018/0049001 A1 | 2/2018 | Volozh et al. |
| 2018/0125623 A1 | 5/2018 | Serval et al. |
| 2018/0168462 A1 | 6/2018 | Pernu |
| 2018/0250108 A1 | 9/2018 | Tamminga et al. |
| 2018/0284745 A1 | 10/2018 | Cella et al. |
| 2019/0005355 A1 | 1/2019 | Joyce et al. |
| 2019/0083215 A1 | 3/2019 | Serval et al. |
| 2019/0200746 A1 | 7/2019 | Serval et al. |
| 2019/0254794 A1 | 8/2019 | Sherman et al. |
| 2019/0254795 A1 | 8/2019 | Sherman et al. |
| 2019/0254796 A1 | 8/2019 | Sherman et al. |
| 2019/0278786 A1 | 9/2019 | Sherman et al. |
| 2020/0089214 A1 | 3/2020 | Cella et al. |
| 2020/0320184 A1 | 10/2020 | Nikitidis et al. |
| 2020/0371491 A1 | 11/2020 | Wong |
| 2021/0153989 A1 | 5/2021 | Huang et al. |
| 2023/0211515 A1* | 7/2023 | Blatter ................ B26B 21/4087 30/41.7 |

FOREIGN PATENT DOCUMENTS

| | | |
|---|---|---|
| CN | 104848861 A | 8/2015 |
| CN | 105832315 A | 8/2016 |
| CN | 106922185 A | 7/2017 |
| CN | 107092894 A | 8/2017 |
| CN | 107153642 A | 9/2017 |
| CN | 107203753 B | 9/2017 |
| CN | 109002189 A | 12/2018 |
| CN | 107516102 B | 10/2020 |
| DE | 4218600 A1 | 12/1993 |
| EP | 3336648 A1 | 6/2018 |
| EP | 3528172 A2 | 8/2019 |
| JP | 2002090267 A | 3/2002 |
| JP | 2009240759 A | 10/2009 |
| JP | 2017187850 A | 10/2017 |
| JP | 2021513415 A | 5/2021 |
| KR | 20130057688 A | 6/2013 |
| WO | 2010024697 A1 | 3/2010 |
| WO | 2014089119 A1 | 6/2014 |
| WO | 2017042673 A1 | 3/2017 |
| WO | 2017165231 A1 | 9/2017 |
| WO | 2019081937 A1 | 5/2019 |

OTHER PUBLICATIONS

All Office Actions; U.S. Appl. No. 16/276,947, filed Feb. 15, 2019.
Dzung Tri Nguyen et al: "SwallowNet: Recurrent neural network detects and characterizes eating patterns", 2017 IEEE International Conference On Pervasive Computing and Communications Workshops (Percom Workshops), IEEE, Mar. 13, 2017 (Mar. 13, 2017), pp. 401-406, XP033092320, DOI: 10.1109/PERCOMW.2017. 7917596[retrieved on May 2, 2017]* II.B, IV, V *.
Extended EP Search Report and Written Opinion for 19157587.7 dated Dec. 10, 2019; 19 pages.
Extended EP Search Report and Written Opinion for 19157587.7 dated Jul. 4, 2019; 17 pages.
Hssayeni Murtadha D et al: "Automatic assessment of medication states of patients with Parkinson's disease usingwearable sensors", 2016 38th Annual International Conference of the IEEE Engineering in Medicine Andbiology Society (EMBC), IEEE, Aug. 16, 2016 (Aug. 16, 2016), pp. 6082-6085, XP032980553, DOI: 10.1109/ EMBC.2016.7592116[retrieved on Oct. 13, 2016].
Inoue, et al., "Deep Recurrent Neural Network for Mobile Human Activity Recognition with High Throughput", In Repository of Xiv:1611.03607, Nov. 11, 2016, 10 pages.
PCT Search Report and Written Opinion for PCT/IB2019/051250 dated Aug. 27, 2019; 20 pages.
Khan, et al., "A Triaxial Accelerometer-Based Physical-Activity Recognition via Augmented-Signal Features and a Hierarchical

(56) References Cited

OTHER PUBLICATIONS

Recognizer", In Journal of IEEE Transactions on Information Technology in Biomedicine, vol. 14, Issue 5, Sep. 2010, pp. 1166-1172.

Langkvist Martin et al: "A review of unsupervised feature learning and deep learning for time-series modeling", Pattern Recognition Letters, vol. 42, Jun. 1, 2014 (Jun. 1, 2014), pp. 11-24, XP028831931, ISSN: 0167-8655, DOI: 0.1016/J.PATREC.2014.01.008 * 3.5 and Figure 4 *.

Ming Zeng, LeT. Nguyen, Bo Yu, Ole J. Mengshoel, Jiang Zhu, Pang Wu, Joy Zhang; "Convolutional Neural Networks for Human Activity Recognition using Mobile Sensors"; 2014 6th International Conference on Mobile Computing, Applications and Services (MobiCASE), 09 Pages.

Natalia Neverova, Christian Wolf, Griffin Lacey, Lex Fridman, Deepak Chandra, Brandon Barbello, Graham Taylor; "Learning Human Identity from Motion Patterns"; Apr. 21, 2016, 10 Pages.

Nicholas D. Lane, Petko Georgiev; "Can Deep Learning Revolutionize Mobile Sensing?" HotMobile'15, Feb. 12-13, 2015, Santa Fe, NM, USA, 06 Pages.

Wang, et al., "Human Activity Recognition with User-Free Accelerometers in the Sensor Networks", In Proceedings of the International Conference on Neural Networks and Brain, Oct. 13, 2005, pp. 1212-1217.

Yousaf Saeed et al: "A Sensor-Augmented Golf Club", a Dissertation submitted to the University of Dublin, Sep. 15, 2006, 88 Pages.

All Office Actions, U.S. Appl. No. 16/276,993, filed Feb. 15, 2019.
All Office Actions, U.S. Appl. No. 16/277,024, filed Feb. 15, 2019.
All Office Actions; U.S. Appl. No. 16/276,972, filed Feb. 15, 2019.

Marcon Marco et al: "Smart Toothbrushes: Inertial Measurement Sensors Fusion with Visual Tracking" In Springer International Publishing, Cham, Nov. 3, 2016, pp. 480-494.

Raffaele et al., Multi-sensor fusion in body sensor networks: State-of-the-art and research challenges, Information Fusion, Sep. 13, 2016, pp. 68-80.

Young-Jae Lee et al: "Toothbrushing Region Detection Using Three-Axis Accelerometer and Magnetic Sensor", IEEE Transactions on Biomedical Engineering, vol. 59, No. 3, Mar. 1, 2012, pp. 872-881.

* cited by examiner

SYSTEM FOR CLASSIFYING THE USAGE OF A HANDHELD CONSUMER DEVICE

FIELD OF THE INVENTION

The present disclosure is concerned with a system allowing the classification of the usage of a handheld consumer device in particular with respect to a target space.

BACKGROUND OF THE INVENTION

It is generally known that the classification of the usage of a handheld user device can be desirable for particular applications. E.g. it was described that the location in the dentition at which a toothbrush is brushing the teeth could be determined by computing the posture of the toothbrush based on data from a triaxial accelerometer and a terrestrial magnetism sensor. This is described in document US 2010/0145654 A1.

There is a general desire to provide a system for classifying the usage of a handheld consumer device that is improved over known systems or that at least provides an alternate solution in view of the known systems.

SUMMARY OF THE INVENTION

In accordance with one aspect, a system for classifying the usage of a handheld consumer device, the system comprising a movable handheld consumer device, the consumer device comprising a sensor unit for determining at least one usage data at successive time instants, the sensor unit being arranged for providing a temporally successive sequence of usage data during a usage session, and an analyzing device being arranged for classifying the usage of the consumer device with respect to at least one set of at least two usage classes relating to different usage properties, the analysis device being arranged for assembling a temporally successive sequence of input tuples of usage data relating to a predetermined time period of the usage session, each of the input tuples having at least one element representing the usage data at the respective time instant, and for inputting the sequence of input tuples into at least one artificial neural network that is arranged to output at least one output tuple that comprises a number of elements in accordance with the number of usage classes, each element of the output tuple representing a prediction value that the usage of the consumer device at the given time instant relates to a respective usage class.

The classification may be performed with respect to a target space comprising a target surface. The handheld consumer device may be arranged for treating the target surface.

In some embodiments, the artificial neural network is arranged to output a sequence of output tuples, in particular a sequence of output tuples having the same length as the sequence of input tuples. A single usage class answer per predetermined time period may be determined based on the sequence of output tuples, e.g. by applying a majority criterion and/or a maximum criterion, in particular after applying an argmax function on each output tuple.

DETAILED DESCRIPTION OF THE INVENTION

Figure 1:
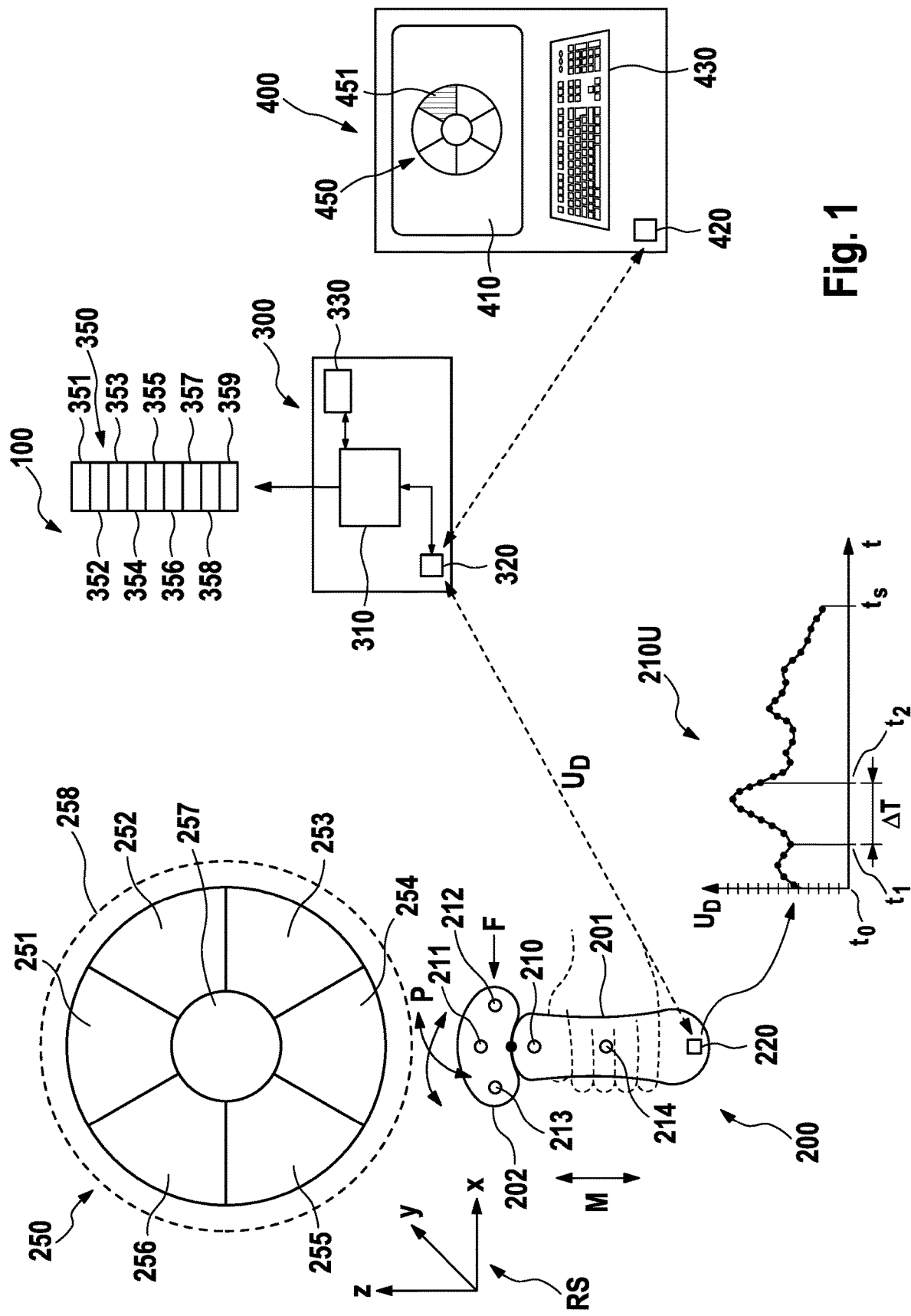
FIG. 1 is a schematic depiction of an example system in accordance with the present disclosure.

The basic concept of the present disclosure is to classify the usage of a handheld consumer device based on a temporal sequence of usage data with respect to a set of usage classes by means of at least one artificial neural network during (or after) a usage session. Several examples in which more than one artificial neural network is used are discussed. A "live" classification (i.e. the classification during the usage session) allows communicating information about the usage to the user while the handheld consumer device is being used, which information may enrich the understanding of the user about the usage and hence may ease or otherwise improve the usage. The subsequent classification allows analyzing the usage of the handheld consumer device during the usage session in a more holistic and complete manner covering the whole usage data information of the completed usage session. Where the live classification may be constricted by the available computing power and the timing of the needed live information, the subsequent (i.e. offline) analysis may balance available computing power with available time. The usage of the handheld consumer device may in particular be classified with respect to a target space comprising a target surface and the handheld consumer device may then be arranged for treating the target surface. The aim is then the classification of the usage of the handheld consumer device in different portions of the target space based on usage data of the handheld consumer device, the usage data in particular comprising at least one of motion data or force data.

A "usage class" is an output class of an artificial neural network (ANN) and is defined by the designer of the ANN. The ANN is learned by inputting labelled input data into the ANN, i.e. input data that is known to relate to one given output class (supervised learning). In a classical example, the ANN is fed with picture data showing a laughing face and the ANN tries to learn those patterns in the picture data that are common for various inputs relating to laughing faces so that a new picture data input can be sorted into the laughing face output class if similar patterns are discovered in the new picture data. In the context of the present disclosure, the usage class relates to the usage of the handheld consumer device and shall differentiate different usage properties. The usage of the handheld consumer device is essentially determined by a temporal sequence of usage data, where the usage data may include at least one of motion data (including orientation data), force data, capacitive data relating to the environment of the handheld consumer device, temperature data, audio data, picture or video data, barometric data, pH data etc. In the present disclosure the main focus is put on usage data that comprises motion (including orientation) data and that may comprise other usage data as well. But it is also considered that the task of classifying the usage of the handheld consumer device can be sensibly approached by only feeding usage data into the artificial neural network that does not comprise any motion data.

Thus, where in the present disclosure reference is made to motion data or motion that is classified with respect to usage classes, it shall be understood that this shall encompass all variants of usage data, in particular such variants that comprise additional sensor data as usage data or where the usage data does not comprise motion data at all.

A "sequence" in the present disclosure means two or more, a "sequence of tuples" means two or more tuples, and a "temporal sequence of tuples" means a sequence of tuples, where the tuples relate to different time instants, where the time difference between successive tuples of the sequence may be equal.

The artificial neural network may receive a sequence of n input tuples of usage data and it may generate any number of output tuples, in particular it may generate one output tuple and up to n output tuples, where any other integer number between 1 and n is possible as well (it is well known that in particular certain artificial networks such as LSTMs may have a one-to-one, one-to-many, many-to-one or many-to-many—in particular a synced many-to-many—architecture). An output tuple is generated by the artificial neural network at a given time instant and thus it is understood that the output tuple relates to this time instant even though the output tuple may comprise information that relates to previous time instants (or future time instants, depending on the concrete architecture of the artificial neural network—see discussion of bidirectional artificial neural networks below) where no output tuple was generated so that the output tuple at the given time instant may basically cover a larger time period.

The usage classes with respect to which the usage of the handheld consumer device shall be classified are combined into at least one set of usage classes. In the classification process, the at least one artificial neural network will provide an output that provides information about the correspondence of the inputted usage data with each of the usage classes, typically one output per time instant for which an input usage data is provided, but this shall not be considered as limiting and it is also considered that the artificial neural network outputs only a single output but receives a sequence of inputs or where a sequence of outputs is provided that is shorter than the sequence of inputs. As was said, the usage classes are defined by the designer of the artificial neural network. The at least one artificial neural network is trained with so-called labelled training data, which is input usage data for which the usage class is known and the artificial neural network will learn to maximize the probability to predict the correct usage class given the input so that the output data is well matched with the input usage data. The idea is that after sufficient training, the artificial neural network will classify new input with respect to the individual usage classes with a sufficiently high prediction probability so that one can reliably refer to the output. In the learning process, weights and biases in the artificial neural network are amended and will typically converge. The more complex the artificial neural network is, the higher is typically the number of the weights and biases used in it (given a size of internal states in the artificial neural network).

The designer of the artificial neural network may define the usage classes with respect to the task that is to be achieved, namely here to differentiate usage data with respect to certain usage properties. One classification task that may be approached is to identify the user of the handheld consumer device from finite group of users, let's say the group of users comprises user A and user B. The abstract usage property is then "usage by user A" and "usage by user B". Once trained, the artificial neural network shall be able to correctly classify usage data from user A as relating to usage class "usage by user A" and usage data from user B as relating to usage class "usage by user B". In another example, the usage classes are defined to differentiate between user types, e.g. "fast users" and "slow users", where fast and slow are the usage properties. This classification is then not limited to a finite group of individual users, but to a finite group of different user types and each and every user in the world will be classified with respect to these two usage classes. A real fast user should then generate an output of the artificial neural network having a high prediction value for usage class "fast user" and similarly, a real slow user shall generate a high prediction value for usage class "slow user". A user that shows both usage properties or none of them will generate much lower and less clearly differentiable prediction values for the two usage classes. Other classification tasks may try to differentiate between a "correct" and an "incorrect" usage or a "good" and a "bad" usage. Getting more abstract, the different usage classes may relate to usages that are typical for using the handheld consumer device in different portions of a target space. E.g. an electric toothbrush can be used to clean different portions of the oral cavities, e.g. the upper jaw and the lower jaw being one possible split of the oral cavity into different portions and each of the potential 32 teeth of the oral cavity (each of the surfaces of each of the teeth) may be another possible, much finer split of the oral cavity into different portions. As will be explained, the usage of the handheld consumer device will be classified with respect to usage in a target space, where the target space may comprise a target surface (e.g. the tooth surfaces and the tongue surface within the oral cavity) and the handheld consumer device may in particular be arranged for treating the target surface. It may be an output of the system described herein to communicate the classification result to the consumer. For the consumer it may be relevant to understand which portion of a target space was currently identified. This will be discussed further below with reference to an example where an electric toothbrush is the handheld consumer device. It shall be noted here that the usage classes used by the artificial neural network may not correspond in a one-to-one and onto manner with the portions of the target space. This will be explained in more detail further below.

Usage classification of handheld consumer devices by means of an artificial neural network have so far not been addressed in a comprehensive manner, in particular not for tasks mapping a device with respect to a target space.

As will be discussed in more detail, the usage of a handheld consumer device may even be better classified if the usage data does not only comprise usage data of one type (i.e. from one type of sensor) but if other usage data is used as well (e.g. motion data and force data or force data and capacitive data etc.). Additional usage data adds at least one further element to the input tuples and thus may improve the prediction quality of the at least one artificial neural network with respect to the output classes. One usage data that was investigated is force data added to motion data (e.g. from at least one of an accelerometer, a gyroscope, and a magnetometer), where the force data relates to a force that is applied at the consumer device, in particular at a consumer device head, during a usage session. A force sensor may be used to measure such force and the force sensor may provide force data having one component, two components or three components (relating to three orthogonal directions). A force sensor may additionally or alternatively also determine the torque in one, two or three directions, e.g. by means of a 6-axis force sensor.

Several example embodiments described herein are focused on the usage classification for toothbrushes, i.e. manual or electric toothbrushes. But the term "handheld consumer device" shall comprise many other consumer devices as well, e.g. wet razors or electric shavers, epilators, hair bushes, massage devices, scrubbers or mops or similar devices.

The usage data is typically generated by at least one sensor located in the consumer device (e.g. in a handle and/or in a head of the consumer device). The at least one sensor may be sampled at a given first frequency to generate a temporally successive stream of raw sensor data. While the sensor data may be forwarded as usage data to the analyzing device (e.g. in a wired or wireless manner) at the first frequency, the raw sensor data may first be processed (e.g. averaged and/or de-noised and/or digitized with a certain resolution such as 16, 14, 12, 10, 8 or 6 bit), where the processing my include a change in the sensor data frequency from the first to a second frequency at which the processed sensor data is then submitted as usage data to the analyzing device. The second frequency may then be lower than the first frequency, e.g. the first frequency may be about 100 Hz or higher (e.g. 200 Hz or 500 Hz or 1 kHz etc.) and the second frequency may be about 100 Hz or smaller, e.g. 50 Hz or 25 Hz etc. The analyzing device may use usage data relating to a given predetermined time period to perform the classification, which predetermined time period is typically shorter than the usual usage session time. This predetermined time period may be in the range of between 0.1 second to 10 minutes (or any value in between), while a typical usage session time period may be in the range of between 10 seconds and 100 minutes (or any value in between). The number of temporally successive usage data (i.e. input tuples) within the predetermined time period may be in the range of between 2 to 1000 (or any number in between), in particular in the range of 5 to 100 or 10 to 50 or 20 to 30 such as about 25. This shall not exclude that the system as described also functions with only a single input tuple instead of inputting a sequence of input tuples.

Artificial neural networks typically use an internal size of states that is higher than at last the size of the input tuples discussed in the present disclosure. A large internal state size generates large sized weight matrices and bias vectors and thus provides a high flexibility to adapt the artificial neural network to the learning data. But in particular if the artificial neural network shall run on a limited performance processor (e.g. on a smartphone), the size of the internal states may not be chosen arbitrarily high. E.g. it was found that a size of about 256 or lower is sufficient for the task at hand and that a larger size will not necessarily lead to an improved prediction possibility.

It is considered in some embodiments that the analyzing device provides only a single output answer per predetermined time period (where a single output answer means that a single usage class is identified as the usage class relating with highest probability to the usage of the consumer device during the predetermined time period). That may mean that the artificial neural network receives a plurality of input tuples and generates only a single output tuple, or it may mean that the artificial neural network provides a sequence of output tuples and the analyzing device further processes the sequence of outputs to provide a single output answer per predetermined time period. It may be one feature of the analyzing device to not provide a usage class as answer in case that the prediction is not credible as expressed by a prediction value below a certain predetermined threshold. In a case where the prediction values are normalized, this threshold may lie in a range of between 0.5 and 0.99, or between 0.6 and 0.9 or between 0.65 and 0.8 or about 0.7.
System for Classifying the Usage of a Handheld Consumer Device FIG. 1 is a schematic depiction of an example system 100 in accordance with the present disclosure. The system 100 comprises a handheld consumer device 200 and an analyzing device 300. An optional presentation device 400 is here part of the system 100; the presentation device may be realized as a screen, a smart speaker, an LED light array etc. While it is shown in FIG. 1 that the handheld consumer device 200 (for sake of simplicity, the term handheld consumer device is herein also abbreviated simply as "consumer device") and the analyzing device 300 are physically separate devices, it shall not be excluded that both are realized within a single housing, i.e. the analyzing device 300 may be incorporated into the consumer device 200, or they may be realized as an integral single device. In other embodiments, the analyzing device is realized as a remote analyzing device, e.g. as a cloud computer.

In the shown embodiment, the consumer device 200 comprises a handle 201 for being grasped by a consumer's hand (a hand is shown in dashed lines) and a treatment head 202 for treating at least a portion of a target space 250. The treatment head 202 is here movable with respect to the handle 201, in particular the treatment head 202 is pivotable in one or two directions with respect to the handle 201 as is indicated by double arrows P. Here, the consumer device 200 comprises a sensor unit comprising an inertial sensor 210 located in the handle 201 and a further inertial sensor 211 located in the treatment head 202. It is noted that a single inertial sensor 210 or 211 is sufficient in accordance with the present description. The inertial sensors 210 and 211 generate motion data relevant to acceleration, angular velocity and/or orientation of the consumer device 200 with respect to a reference coordinate system RS, which is indicted in FIG. 1 as having three coordinate axes x, y, and z. As one example, the nine-axis inertial sensor BMX160 from Bosch Sensortec, Germany, may be used to realize the inertial sensor. In accordance with at least one aspect, a consumer device in accordance with the present description comprises a sensor unit with at least one inertial sensor providing at least one temporally successive stream of motion data with respect to at least one axis. The consumer device 200 as here shown has a sensor unit that comprises a further sensor 212, which is arranged as a force sensor that determines a force F that is applied at the consumer device 200 (in particular at the treatment head 202 of the consumer device 200) along at least one axis. Additionally or alternatively, a force applied at the consumer device may be determined by monitoring the current flowing through a drive unit of the consumer device or by determining the noise of, e.g., the inertial sensor data. The sensor unit of the consumer device 200 here also comprises a capacitive sensor 213 that is disposed at the treatment head 202 in order to determine changes in the environment of the treatment head 202. The sensor unit of the consumer device 200 may comprise further sensors, e.g. a further capacitive sensor 214 that determines changes in the environment of the handle 201. The sensors 212, 213, or 214 may provide a temporally successive stream of sensor data different to motion data. The sensor data from at least one of these sensors 212, 213, 214 may be combined with the temporally successive data stream of the at least one inertial sensor 210, 211 and may be transmitted as usage data Up to the analyzing device 300, which in the shown embodiment happens in a wireless manner via a transmitter or transceiver 220. Both, motion data generated by the inertial sensors 210 and 211 and further data generated by the further sensors 212 to 214 are considered as "usage data" that characterizes usage of the consumer device 200 in a given period of time. The consumer device 200 may be arranged to store the usage data and to transmit it only after the end of a usage session.

It is noted here, that a sensor unit of a consumer device in accordance with the present disclosure comprises at least one sensor for generating usage data. In some embodiments the at least one sensor is an inertial sensor, in some embodiments the at least one sensor is a sensor that provides usage data not being motion data. In accordance with at least one aspect of the present disclosure, the system 100 utilizes usage data from the non-inertial sensors and may optionally combine non-inertial sensor data with inertial sensor data for the task of classifying the usage of the consumer device 200.

The consumer device 200 may be intended to be used in at least portions of a target space 250. The target space 250 is here schematically shown to comprise seven portions or locations 251 to 257 and also another portion 258 that is indicated by a dashed line and which will be discussed in more detail further below. In some embodiments, the target space 250 may represent at least a portion of the real 3D space in which the consumer device 200 may be used, where in particular at least one of the portions 251 to 258 may represent a portion of a target surface on which the consumer device is intended to be used.

The analyzing device 300 here comprises a receiver or transceiver 320 for at least receiving the usage data Up from the consumer device 200. In embodiments, where the consumer device and the analyzing device are realized as a physically integral device, the data transfer may happen just per a wired connection (or the consumer device 200 may comprise contacts for establishing a wired connection with another device, e.g. a base station or an analyzing device etc.). As was said, the sensor unit comprising the at least one sensor 210, 211, 212, 213, 214 provides usage data $U_D$ that may include motion data as a temporal sequence of data tuples (the term tuple as used herein means a finite ordered list (sequence) of elements and n-tuple means such a list having n elements). As was explained, the motion data may comprise at least one motion data per time instant, typically three or more, such as four, five, six, seven, eight, or nine motion data per time instant. The usage data $U_D$ may thus be arranged as respective n-tuples per time instant. Additional usage data $U_D$ such as force data from at least one further sensor 212 may be added to the motion data so that respectively larger n-tuples of usage data $U_D$ are available per time instant. Typically, a sequence of n-tuples of usage data Up representing a predetermined period of time is inputted into a processing unit 310 for processing the usage data $U_D$ by means of an artificial neural network in order to classify the usage data Up with respect to a set 350 of usage classes 351 to 359. While in some embodiments, the usage classes 351 to 359 are independent from the target space 250 (e.g. the usage classes relate to different user types or to correct vs. incorrect usage), the usage classes 351 to 359 may in some embodiments be associated with the portions 251 to 258 of the target space 250 as at least some of the usage classes 351 to 359 relate to usage of the consumer device 200 in certain portions 251 to 258 of the target space 250. As will be explained in more detail below, the relationship between the usage classes 351 to 359 of the set of usage classes 350 and the portions 251 to 258 of the target space 250 may then be arbitrary (i.e. may deviate from a bijective relationship). This means for example that a first usage class 351 may be associated with one portion 251 of the target space 250, one usage class 352 may be associated with two portions 251 and 252 of the target space 250 so that two usage classes 351 and 352 are associated with one portion 251 of the target space 250 and one usage class 359 is not associated with any portion of the target space 250. As a non-limiting example, the number of usage classes may be 20 while the number of portions of the target space may be 6.

The analyzing device 300 may comprise a storage unit 330 for storing the received usage data and/or data generated in the classification procedure (to have the data available for later tasks such as comparing previous outcomes with current outcomes or for presenting a history of outcomes) and/or for storing program routines or look-up tables or the like.

As was explained, the usage data $U_D$ of a given time period will be used by the system 100 to classify the usage of the consumer device 200 during the time period. The usage of the device may in particular be determined based on the motions made by consumer device 200 and which motions are particular for treatment of a particular portion of the target space 251 to 257 (which may be portions of the target surface) or are particular for a transitional motion.

A schematic depiction of usage data $U_D$ outputted by, e.g., the inertial sensor 210 or by the force sensor 212, is shown as graph 210U, where the usage data $U_D$ is schematically shown as a function of time t. The depicted graph shows by way of example the value of $U_D$ during a usage session that starts at t0 and ends at $t_s$. The system 100 may be used to classify the usage of the consumer device 200 in a predetermined time period $\Delta T$ that starts at time instant $t_1$ and ends at time instant $t_2$ based on the usage data $U_D$. The classification may repeat the classification for the subsequent time period. A usage session may have a length in the range of between 1 second and 100 minutes and the time period $\Delta T$ may have a length in the range of between 0.1 second and 10 minutes.

An optional presentation device 400 is shown in FIG. 1 as a part of the system 100. While the presentation device 400 is here shown as a physical separate device that is separate from the consumer device 200 and the analyzing device 300, it shall be understood that the presentation device may be incorporated into either the consumer device 200 or the analyzing device 300 or all devices may just be realized as one integral device. In the shown embodiment, the presentation device 400 has a display 410 for displaying visual information to a user in a live or offline manner, a receiver or transceiver 420 for at least receiving data from the analyzing device 300, and a user interface 430, which may be realized as a touch keyboard, as a mechanical keyboard or as a voice interface. It is here indicated that the presentation device 400 may show a visual representation of the set of usage classes or of the target space 450 on the display 410 and one portion 451 of the visual representation of the set of usage classes or the target space 450 is highlighted to indicate to the user that the system 100 has classified the usage data of the consumer device 200 to be associated with the highlighted portion 451.

Handheld Consumer Device

Figure 2:
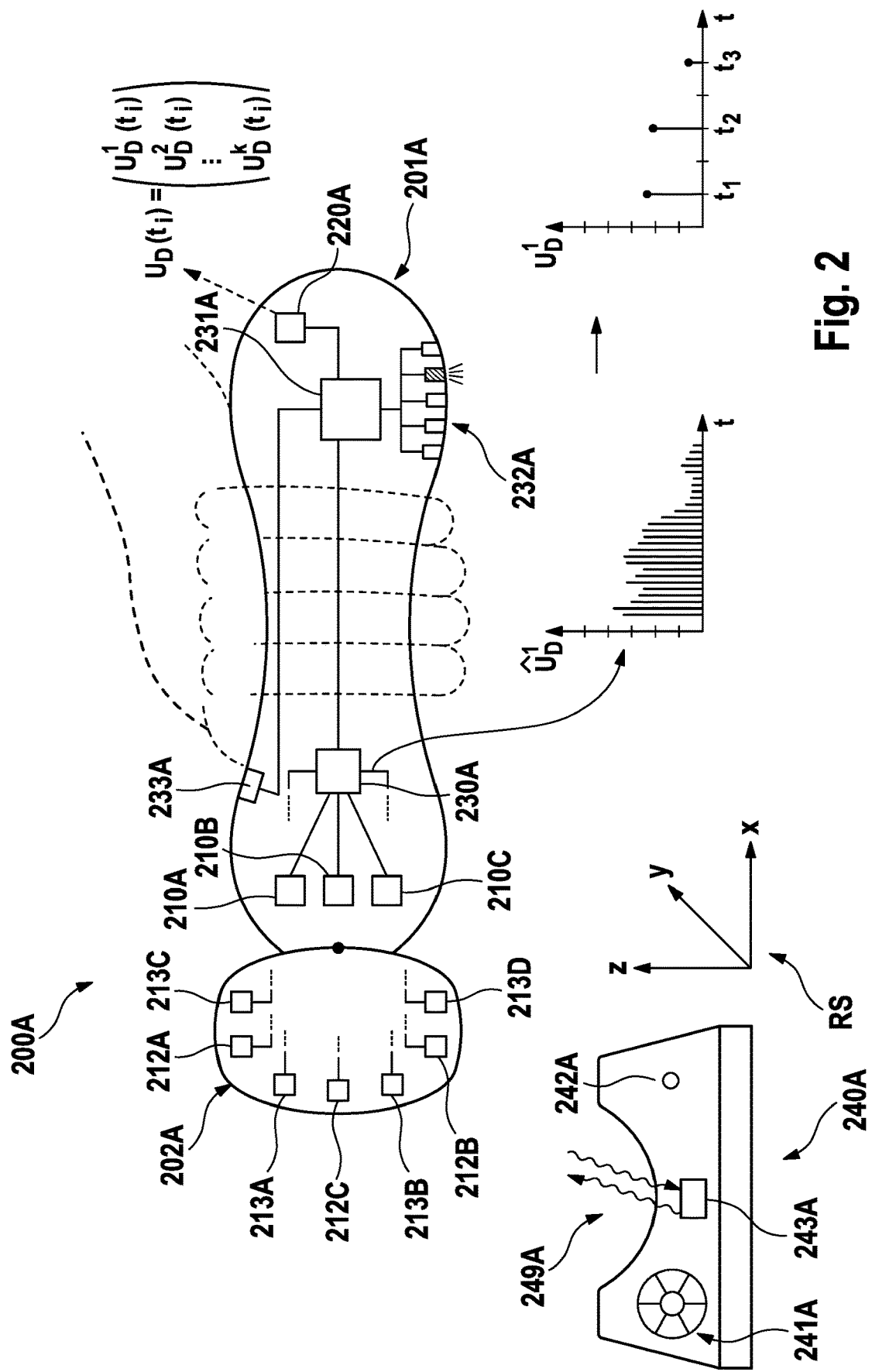
FIG. 2 is a schematic depiction of an example handheld consumer device in accordance with the present disclosure.

FIG. 2 is a depiction of an example consumer device 200A in accordance with the present disclosure. As is shown, the consumer device 200A may have a base station 240A, which may, e.g., have charging functionality but may also only serve to mechanically hold the consumer device 200A in a receptacle 249A.

The consumer device 200A may comprise at least one inertial sensor 210A, 210B, 210C and this at least one inertial sensor 210A, 210B, 210C may be at least one of an accelerometer, gyroscope, or magnetometer as already discussed. It is here shown that the at least one inertial sensor 210A, 210B, and 210C is disposed in a handle 201A of the consumer device 200A. Alternatively or additionally, one or more inertial sensors may be disposed in the treatment head 202A of the consumer device 200A, in particular in case the treatment head 202A is arranged to be movable with respect to the handle 201A. In the shown embodiment, the consumer device 200A has at least one further sensor 212A, 212B, 212C, 213A, 213B, 213C, or 213D located in the treatment head 202A. This at least one further sensor may be, e.g., realized as a force sensor, a capacitive sensor, a temperature sensor, a barometric sensor etc. The consumer device 200A may comprise two or even more further sensors 212A, 212B, 212C, 213A, 213B, 213C, or 213D, e.g. two or more capacitive sensors may be disposed in different parts of the treatment head 202A to determine changes in the dielectric environment of the treatment head 202A in different areas. Alternatively, the consumer device 200A does not comprise any inertial sensors. As one example for a barometric sensor, an InvenSense ICP-10100 sensor from TDK Corporation, Japan, is able to detect height differences of about 5 cm and may thus sensibly contribute usage data for the various types of consumer devices considered herein.

The inertial sensor 210A, 210B, 210C and/or the further sensors 212A, 212B, 212C, 213A, 213B, 213C, or 213D may be coupled with a sensor processing unit 230A. The sensor data processing unit 230A may be arranged to receive sensor data $U_D$ from the at least one inertial sensor 210A, 210B, 210C and/or the at least one further sensor 212A, 212B, 212C, 213A, 213B, 213C, or 213D at a first frequency, which may be a high frequency, e.g. above 100 Hz and the sensor data processing unit 230A may then be arranged to process the received sensor data $\hat{U}_D^1$ and to output processed sensor data $U_D^1$ at a second frequency that is a lower frequency, e.g. below 100 Hz, as is indicated in two graphs showing $\hat{U}_D^1$ and $U_D^1$ as a function of time t. The sensor data processing unit 230A may process the received sensor data $\hat{U}_D^1$ by applying, e.g., an averaging filter or the like to generate the low frequency sensor data $U_D^1$. In particular when the consumer device 200A is physically separate from an analyzing device (see FIGS. 1 and 3), the low frequency sensor data $U_D^1$ may support the live analysis due to reduced data rate that is to be transmitted from consumer device 200A to the mentioned analyzing device. The consumer device may comprise a transmitter or transceiver 220A to establish a wireless connection with the analyzing device, e.g. based on Bluetooth or Bluetooth LTE or any other wireless data exchange format. The consumer device 200A may comprise a processor unit 231A for at least storing sensor data, e.g. in order to allow a later transmission of the sensor data $U_D^1$ to an analyzing device. In some embodiments, the processor unit 231A may perform an analysis of the sensor data $U_D^1$ without the need of a further analyzing device, i.e. the analyzing device/the functionality of the analyzing unit may be incorporated into the consumer device 200A. In order to provide feedback or at least information to the user, the consumer device 200A may comprise a feedback unit 232A, which in FIG. 2 is indicated as a number of visual light elements, e.g. LEDs, where each light element may be assigned to a certain portion of the target space (e.g. portions of the oral cavity), so that the consumer device 200A can provide feedback about the usage class that is identified or about a portion of a target space that is associated with the respective usage class. A consumer device 200A may also provide user feedback via, e.g., a drive unit of the consumer device 200A. E.g. the drive unit may provide a particular vibration pattern to communicate certain feedback to the user, e.g. to indicate that the currently treated surface portion has received sufficient treatment and that the consumer may move towards another surface portion. The consumer device 200A may also comprise a user interface 233A allowing the user to provide input such as a request to start an offline analysis of stored sensor data.

The (potentially processed) sensor data $U_D^1$ from the at least one inertial sensor 210A, 210B, 210C and/or from the at least one further sensor 212A, 212B, 212C, 213A, 213B, 213C, or 213D may be transmitted to a physically separate analyzing device by means of, e.g., the transmitter or transceiver 220A as a temporal sequence during a usage session or after a usage session, i.e. sensor data $U_D (t_i)$ is transmitted, where $U_D (t_i)$ stands for a k-tuple of sensor data elements as is indicated in FIG. 2 by stating that $U_D (t_i) = \{U_D^1(t_i), U_D^2(t_i), \ldots, U_D^k(t_i)\}$, where k is the number of individual sensor data, e.g. where k=3 may stand for the three elements of sensor data from a three-axis accelerometer, k=6 may stand for the six elements of a six-axis inertial sensor comprising a three-axis accelerometer and a three-axis gyroscope, and k=7 may stand for the same as before but extended by data from a single-axis force sensor. Obviously, the number k of elements of the temporal sequence of -tuples depends on the number of individual sensor data that shall be used for the usage classification purpose.

The temporal sequence of sensor data $U_D (t_i)$ is submitted during a usage session for live usage classification with only a very short delay between the generation of the data and their transmission. The sensor data may also be squeezed into a certain data length, e.g. the sensor data may be transmitted as digital data having a certain length such as 8 bit or 10 bit or 12 bit or 16 bit or 20 bit etc. The reduction of the typically analogue sensor data on digitized sensor data having a limited resolution may be helpful for allowing the live sensor data transmission in case of a limited data transmission rate. It had been found that for a typical classification task for a consumer device such as an electric toothbrush, a resolution of the sensor data of 8 bit is sufficient and higher resolutions do not lead to a noticeable increase in the final prediction quality of the usage classification task. The sensor data may be raw sensor data or pre-processed sensor data.

For offline usage classification, the sensor data may be stored with high resolution (e.g. 24-bit resolution) and optionally also with high sampling rate (e.g. 200 Hz) and the same high-resolution sensor data may then later be transmitted for analysis as transmission time and limitations in data transmission rate are less relevant for offline usage classification. The storage in the consumer device 200A may be sized to allow storing one, two, five, ten, twenty, one hundred etc. usage sessions so that the user may start an offline usage classification only after a certain time of using the consumer device 200A.

The consumer device 200A may be placed on a base station 240A, in particular the consumer device 200A may be mechanically held in a receptacle 249A of the base station 240A (holding of the consumer device 200A may happen via to a positive fit provided by the receptacle or the base station may comprise a magnet and the consumer device 20A may comprise a magnet or magnetizable element as well). The base station 240A, which may have a charging functionality to charge a rechargeable accumulator disposed in the consumer device 200A while the consumer device 200A is placed on the base station 240A, may comprise a transmitter or transceiver 243A for transmitting data to an analyzing device (see FIG. 3), which analyzing device may be realized by a remote processing device (e.g. a cloud computer). The transmitter or transceiver 243A may then have a WiFi communication capability, e.g. WLAN. The base station 240A may be arranged to establish a wired or wireless communication link with the consumer device 200A (e.g. based on Bluetooth™ or Bluetooth™ LTE). A wired communication may be established when the consumer device 200A is placed on the base station 240A. The consumer device 200A may then not need to have its own transmitter or transceiver 220A for transmitting sensor data (and other data), but this can be handled by the base station 240A. In some embodiments, the base station 240A may also realize the analyzing device and may thus comprise the functionality as will be explained for the analyzing device 300A with reference to FIG. 3 further below. Whether or not the base station 240A realizes the analyzing device, it may comprise a means to communicate feedback to the user, e.g. a visual feedback unit 241A or an audible feedback unit 242A. E.g. an analyzing device or the consumer device 200A may send the results of the usage classification to the base station 240A and the results may then be shown by means of the visual feedback unit 241A or be communicated via the audible feedback unit 242A.

Analyzing Device

Figure 3:
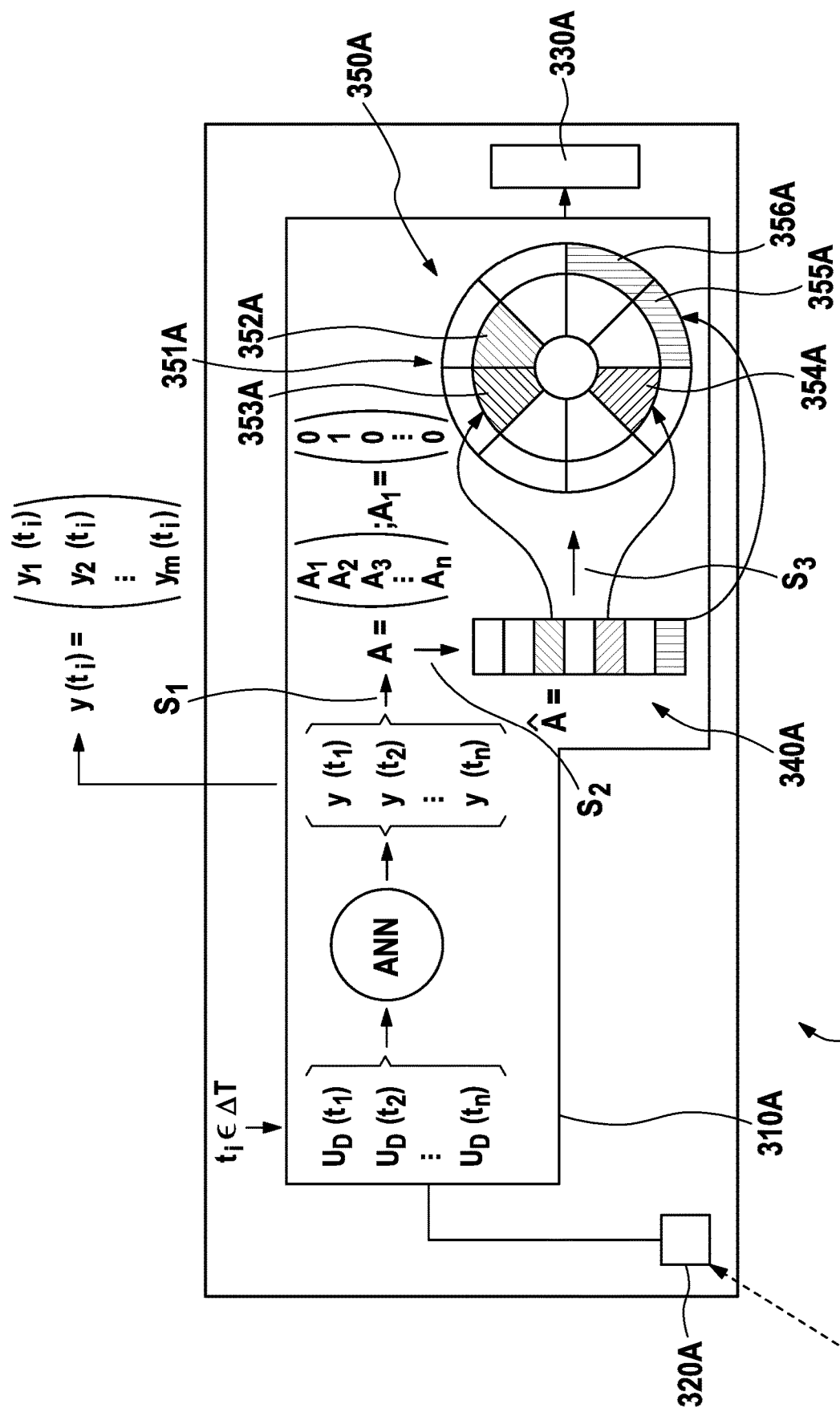
FIG. 3 is a schematic depiction of an example analyzing device in accordance with the present disclosure.

FIG. 3 is a schematic depiction of a physically separate analyzing device 300A that is part of a system in accordance with the present disclosure. As was already discussed, the same functionality as described here with respect to a physically separate analyzing device 300A may be incorporated into the consumer device or into a base station or presentation device or into a remote computing device such as a cloud computing device. The analyzing device 300A may comprise a receiver or transceiver 320A, a processing unit 310A and a storage unit 330A. The temporal stream of sensor data tuples $U_D(t_i)$ is received via the receiver or transceiver 320A and is fed into the processing unit 310A. The processing unit 310A may collect a certain number of sensor data tuples $U_D(t_i)$ that relate to a predetermined period of time $\Delta T$, where it is indicated in FIG. 3 that a number of n such k-tuples of sensor data $U_D(t_i)$, $i \in [1,n]$, are collected and then fed into the usage classification portion of the processing unit 310A. The usage classification is here done by means of at least one artificial neural network ANN. The details of such at least one artificial neural network will be explained in detail in several of the following chapters. As is known in the art, the previously trained artificial neural network ANN receives the sequence of n sensor data tuples $U_D(t_i)$, $i \in [1,n]$, that relate to the relevant period of time $\Delta T$ and outputs a at least one output or answer tuple. It is here shown as a non-limiting example that a sequence of n output tuples $y(t_i)$, $i \in [1,n]$, is provided, where the each of the answer tuples has m elements as is indicated in FIG. 3 by $y(t_i) = \{y_1(t_i), y_2(t_i), \ldots, y_m(t_i)\}$, where the integer m is the number of usage classes with respect to which the input shall be classified. Each element $y_j(t_i)$, $j \in [1,m]$, then is a number that is associated with the prediction that the sensor data inputted into the artificial neural network ANN at time instant $t_i$ relates to usage class j (i.e. the higher the value, the better the prediction). As will be explained further below, the output of the artificial neural network ANN may be normalized by a softmax function so that the elements of each m-tuple $y_j$ are squeezed into the range [0, 1] and add to 1. Such normalized values may be said to relate to a probability that the respective input relates to usage class j.

The processing unit 310A may be arranged to process the sequence of output tuples in order to arrive at a single usage class answer that relates to the currently assessed time period $\Delta T$. In this processing step, each output tuple $y(t_i)$ may be transformed into a simple answer tuple $A_i$ so that a sequence of simple answer tuples $A = \{A_1, A_2, \ldots, A_n\}$ results. For example, if m=5 and the normalized output tuple is $y_i(t_i) = [0.1, 0.1, 0.6, 0.15, 0.05]$, then the element of the output tuple having the highest value is the third element and a simple answer tuple $A(t_i) = (0, 0, 1, 0, 0)$ may be provided. Instead of providing a n-tuple, an argmax function can be applied on each output tuple $y(t_i)$ and the simple answer tuple would then be a scalar value (a 1-tuple), namely $A(t_i) = 3$ in the present example. The non-limiting example given in FIG. 3 builds on the realization that each answer tuple is a vector or n-tuple of which only one element is a 1 and the other elements are 0. In the art of neural networks, the argmax function may be considered as the more usual way of processing the output tuples.

The processing unit 310A may then be arranged to reduce the sequence of simple answer tuples $A = \{A_1, A_2, \ldots, A_n\}$ to a single usage class answer $\hat{A}$. This reduction may happen by applying a maximum criterion or majority criterion onto the sequence of simple answer tuples A. In the example where the simple answer tuples $A_i$ are m-tuples, a maximum criterion may mean that only the k-th element of the m elements of the single usage class answer $\hat{A}$ is set to 1 if most k-th elements of the simple answer tuples $A_i$ are a 1 and element k is set to a 1 when a majority criterion is applied if at least 50% of the k-th elements 1 of the simple answer tuples $A_i$ are a 1. The element that is set to 1 then corresponds to the usage class that the system has identified as best fitting the input from the predetermined time period. All other elements of the single usage class answer $\hat{A}$ are then 0. In case none of the elements of the single answer tuple $\hat{A}$ is a 1, then the response of the artificial neural network was not reliable, and no classification has happened, i.e. no usage class will be provided as output. Alternatively, the simple answer tuples $A(t_i)$ may be scalar values as a result of an argmax function, where the values coincide with the element of the output tuple $y(t_i)$ that has the highest prediction value. The single usage class answer $\hat{A}$ may then also be a scalar value, the value indicating the usage class that the system has identified as best fitting the input from the predetermined time period, e.g. $\hat{A} = 3$. In summary, the processing unit 310A may be arranged to provide a single usage class answer of the artificial neural network ANN for the currently assessed time period $\Delta T$. The processing unit 310A may be arranged to provide no answer in case the prediction probability is not reliable (e.g. in case a threshold was applied and/or no majority was identified etc.).

As was already discussed, the usage classes may be directly and unambiguously associated in a one-to-one and onto manner (i.e. in a bijective manner) with portions of the target space. But there may also be a more complex association of the usage classes with the portions of the target space. E.g. in case the consumer device is an electric toothbrush, the usage classes may relate to different motions of the electric toothbrush. Usage class 1 may relate to motions typical for brushing the buccal surfaces of the upper left molars, usage class 2 may relate to motions typical for brushing the buccal surfaces of the lower left molars, and usage class 3 may then relate to motions typical for brushing the buccal surfaces of the left molars, i.e. of the upper and lower left molars in a single movement. Hence, the processing unit 310A may be arranged to map the usage class that is identified for the currently assessed time period $\Delta T$ onto the portions of the target space, where here a graphical representation of the target space 350A is shown that may also represent a visual feedback to the user via a display. In the example as shown, the third usage class (which is provided as answer if the third element of the single answer tuple $\hat{A}$ is a 1) may relate to two portions 352A and 353A of the target space 350A, together combined into portion 351A. The first element of the single usage class answer $\hat{A}$ (i.e. the first usage class) may then be associated with portion 352A and the second element (i.e. the second usage class) with portion 353A (this also holds if $\hat{A}$ is a scalar value and $\hat{A}$=1). Usage class number five may be associated with portion 354A of the target space, which may relate to motions typical for brushing the lower right molars (e.g. $\hat{A}$=5). And usage class number seven (e.g. $\hat{A}$=7) may be associated with portions 355A and 356A of the target space 350A, which portions 355A and 356A indicate that the toothbrush was not used for brushing but was moved from one brushing area to another (i.e. a transition motion). Similar examples can be provided for other consumer devices such as electric shavers, mops etc. The target surface for an electric shaver may e.g. be the head of a subject.

Where in the previous discussion the term "motion" was used, this relates to cases where only motion data are inputted as sensor data. In case the usage data comprise other or additional sensor data than motion data, the term motion is to be replaced by the term "usage".

Example System Comprising an Electric Toothbrush

Figure 4:
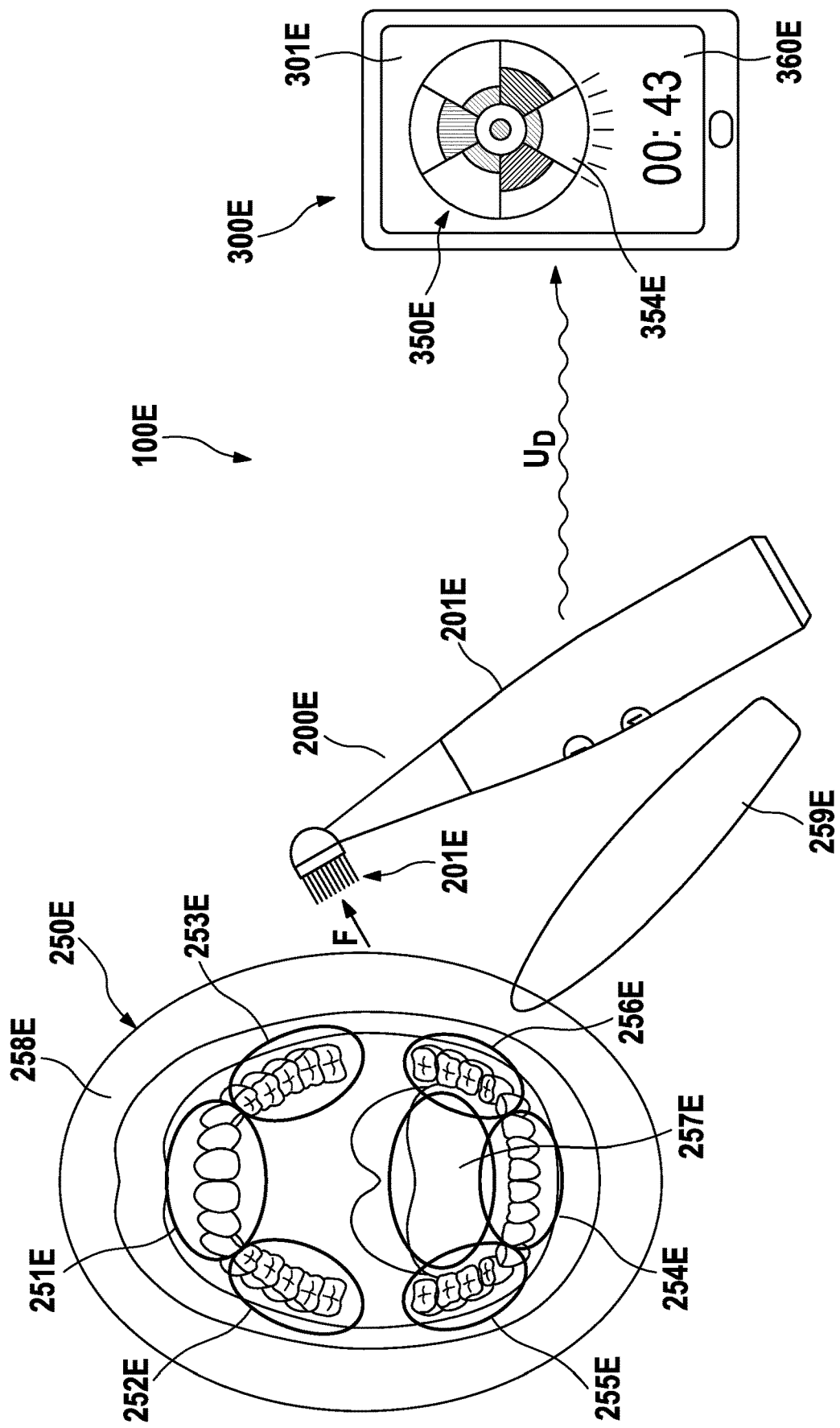
FIG. 4 is a depiction of an example system in accordance with the present disclosure where the consumer device is an electric toothbrush and the analyzing device is a smartphone.

FIG. 4 is a schematic depiction of an example system 100E comprising a consumer device 200E realized as an electric toothbrush and an analyzing device 300E that is realized as a smartphone and that in the present case also realizes the functionality of a presentation device.

As is generally know, the electric toothbrush 200E comprises a handle 201E and a treatment head 202E, namely a brush head and the electric toothbrush 200E is intended to clean portions of the oral cavity including the teeth and optionally the tongue. Hence, a target space 250E of the electric toothbrush 200E comprises portions 251E to 256E that here relate to the teeth and a portion 257E that relates to the tongue. In addition, the target space 250E comprises here two further portions 258E and 259E that relate to transition motions of the electric toothbrush head, i.e. motions that do not relate to brushing but to moving the toothbrush from one tooth/teeth section to another tooth/teeth section. The number of portions of the target space used here to separate the oral cavity into individual portions is merely an example and shall be considered as non-limiting. In other embodiments, the target space comprises just one portion relating to the teeth and one portion that relates to transition motions. In another example, every molar is split into three portions that relate to buccal, lingual, and occlusal surfaces of each of the molars and each incisor is separated into two portions that relate to buccal and lingual surfaces (i.e. in total 84 portions, each portion relating to one surface of a particular tooth). The tongue may also be split into two or more portions, e.g. a front portion and a back portion. This shall just indicate that the target space may have any sensible number of portions.

The electric toothbrush 200E here comprises sensors as already discussed and is arranged to transmit during a usage session a temporal sequence of usage data $U_D$ to the analyzing device 300E. The analyzing device 300E is arranged to perform a classification of the usage of the electric toothbrush 200E with respect to a set of usage classes by means of an artificial neural network and to map the resulting usage class onto the target space 250E so that on a display 301E of the analyzing device a visual representation 350E of the target space 250E can be shown. Here, the visual representation 350E comprises seven portions (the transitions are not visually indicated). As an example, each of the visually depicted visualizations is filled to a certain level so that the user can easily see how many percent of recommended brushing activity was already spent in which of the relevant portions of the target space. Further, visually depicted zone 354E is highlighted to indicate the currently brushed portion of the target space (i.e. of the oral cavity) based on the result of the assessment of a temporal sequence of usage data $U_D$. As an example, the total brushing time is indicated as another information 360E on the display 301E.

In the following chapters of the description, artificial neural networks and particular artificial neural networks of relevant architecture are shortly described to the extent relevant for the system described herein.

Artificial Neural Networks

An artificial neural network (ANN) is a network of artificial neurons, which use a model of a neuron motivated from neuroinformatics, in which a plurality of inputs is weighted and outputted by means of an activation function. A bias value (or threshold value) may be added to shift the weighted input prior to the activation. Typical activation functions of an ANN are non-linear and monotonically increasing functions such as the sigmoid function or the hyperbolic tangent function denoted as tan h.

Figure 5:
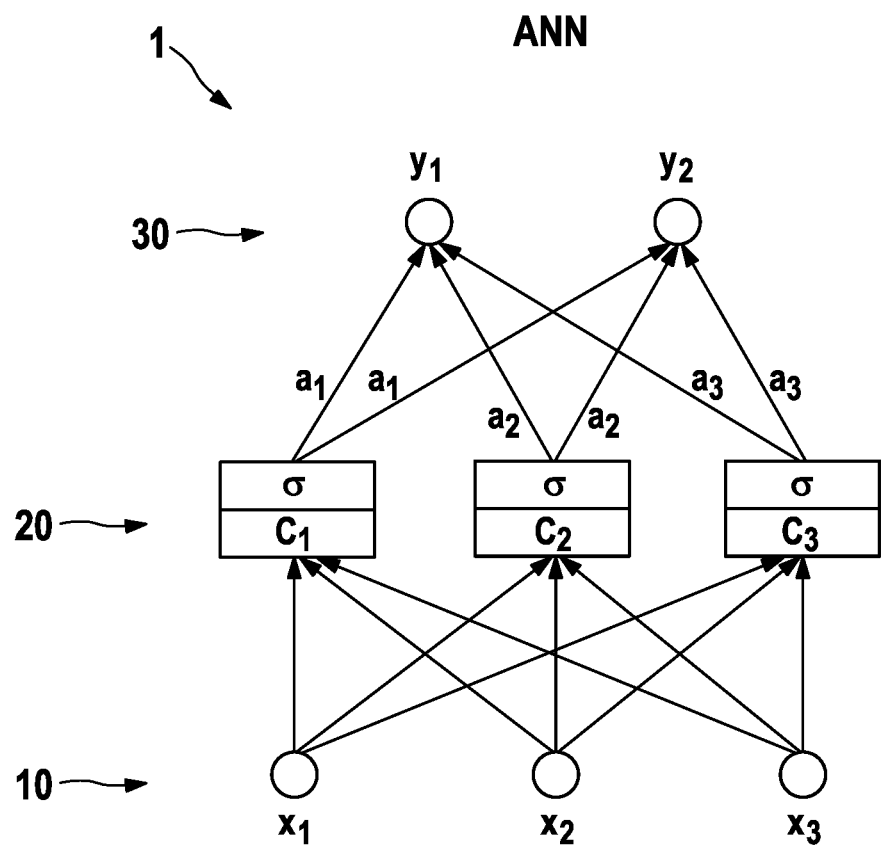
FIG. 5 is a schematic depiction of an artificial neural network architecture.

FIG. 5 is a schematic depiction of an example artificial neural network 1 having an input layer 10, a hidden layer 20 and an output layer 30. The input vectors $x_i$ of the ANN may each be an n-tuple, where n may be any integer number. In accordance with the ANN as shown in FIG. 5, the input vectors $x_i$ are concatenated and the concatenated vector is then fed into each of the units of the hidden layer 20. By means of a fully connected layer the input $c_i=(x_1, x_2, x_3)$ may be transferred into a tuple of any other dimension, e.g. into a k-tuple $\tilde{c}_i$, i=1, 2, 3, and $$\tilde{c}_{ik} = \sum_{j=0}^{3n} w_{ikj} c_{ij} + b_{ik},$$

where $w_{ikj}$ are the elements of the weight matrix for hidden unit i, i=1, 2, 3, and $b_{ik}$ are the elements of the bias vector for hidden unit i, i=1, 2, 3, and j denotes the running index for the elements of the concatenated vector $c_i$ and k denotes the running index for the elements of the k-tuples $\tilde{c}_i$. The weighted output $\tilde{c}_i$ is then outputted by means of the activation function, $a_i=\sigma(\tilde{c}_i)$, where here $\sigma$ represents the sigmoid function. After this activation has happened in the hidden layer 20, the activation vectors $a_i$ may be mapped by a fully connected output layer 30 onto a number of output tuples $y_i$, i=1, 2, of any other dimension, typically having the dimension that coincides with the possible answers of the ANN, e.g. the number of words the ANN shall recognize.

In one typical example and without reference to FIG. 5, an ANN is used to learn a task, e.g. to identify handwritten letters. The weights and biases of the ANN may then be learned by providing so-called labelled input to the ANN, e.g. data streams representing pictures having 50 times 50 pixels (e.g. each pixel representing either black or white) where each picture comprises a hand-written letter to which the answer is known such as letter "c". The initial weights and biases of the ANN are then modified in the (here: supervised) learning process based on the difference between the output of the ANN and the output the system should ideally have provided by means of so-called back-propagation, where in the present example answer "c" the ANN may provide an output vector having 26 elements (one for each letter of the Latin alphabet), where ideally the third element would be a 1 and all others would be zeros). Typically, an ANN may show some convergence in the changes that are applied to the weights and biases if the ANN is sufficiently trained. It may be considered a challenge of the designer of the ANN to find an architecture of the ANN that particularly suits the task to be learned so that the prediction quality of the ANN is sufficiently good and can indeed be used, e.g. in automated handwriting recognition.

As was already mentioned, the task under discussion in this disclosure is to determine a usage class and potentially based on the usage class a portion of a target space in which the handheld consumer device is currently used. It was found that an ANN, in particular certain architectures of an ANN that are discussed further below, can be used to solve this task with sufficient prediction accuracy, if usage data comprising e.g. motion data of the handheld consumer device is used as input into the ANN and the prediction quality may be further improved by adding additional usage data as input into the ANN, e.g. by adding force sensor data that represent the force that is applied at the handheld consumer device, in particular the force that is applied at a treatment head of the handheld consumer device. It is also contemplated that an ANN may be used to solve the provided task by providing usage data as input to the ANN that do not comprise motion data, but only other sensor data such as one-axis or multi-axis force data, data from capacitive sensors disposed at the handheld consumer device, temperature sensors etc. Sensors for providing such usage data have already been discussed.

Recurrent Neural Networks

Figure 6A:
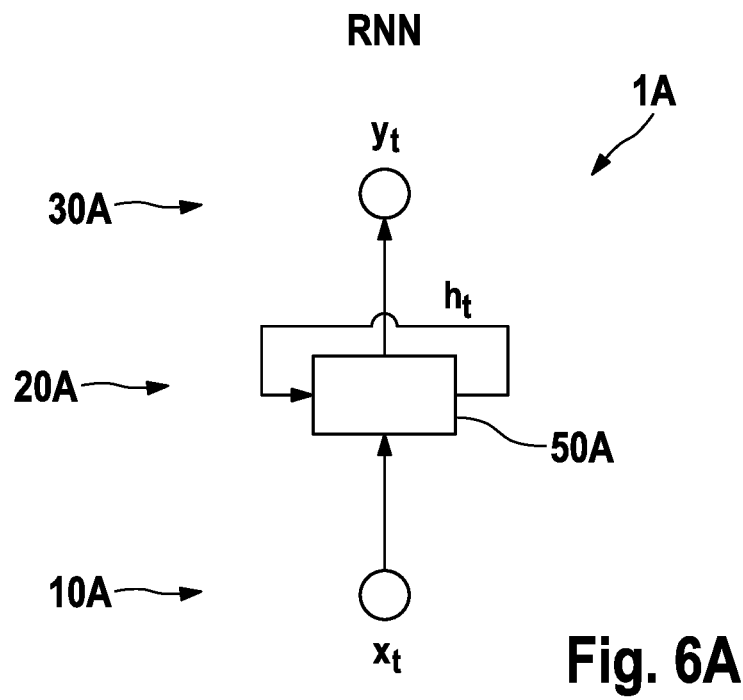
FIG. 6A is a schematic depiction of a recurrent neural network.

Recurrent neural networks (RNNs) are a class of ANNs that have a particular property, namely a recurrent input. FIG. 6A is a schematic depiction of an RNN 1A that comprises an input layer 10A, a hidden layer 20A, and an output layer 30A. It can be seen that the recurrent unit 50A does not only receive an input $x_t$, but also receives a hidden state from the prior time instant, where the hidden state $h_t$ of the current time instant t is then inputted into the neural unit 50A for computing the output of the next time instant t+1.

Figure 6B:
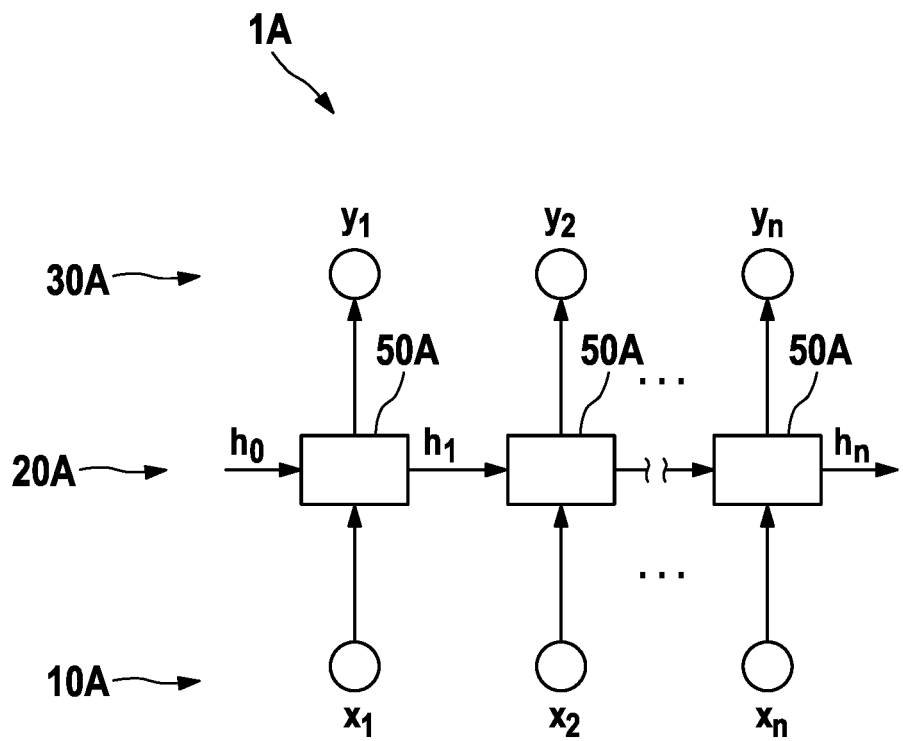
FIG. 6B is a schematic depiction of the recurrent neural network shown in FIG. 6A in its unrolled or unfolded state.

FIG. 6B is a schematic depiction of the RNN of FIG. 6A in its "unrolled" or "unfolded" state. The resulting chain of recurrent neural units 50A is applied at different "time instants" t, where t=[1,n]. At the first time instant, t=1, the neural unit 50A receives the initial hidden state $h_0$ and the input $x_1$ to compute the output $y_1$ and the modified hidden state $h_1$, which is then fed into the neural unit 50A at the next time instant, t=2. The neural unit 50A receives at time instant t=2 the input $x_2$ and, as mentioned, the hidden state $h_1$ to compute the output $y_2$ and the hidden state $h_2$. This chain continues until the end of the input sequence at time instant t=n. The particular benefit of the hidden state is to carry along a memory over time. As an example, the neural unit 50A may in a simple realization just be a tan h activation function, i.e. the hidden state $h_{t-1}$ and the input $x_t$ are concatenated and are activated by the tan h function after having gone through a fully connected layer as was already explained with respect to ANN units. As is clear from FIG. 6A, the weights and biases of the neural unit 50A do not change as a function of time.

The structure of an RNN is suitable for treating sequential data. While the term "time instant" used herein may be interpreted broadly and may not necessarily relate to real time, it was found that the task of classifying the usage of the handheld consumer device can be approached by providing, e.g., motion data and/or other usage data as a real time sequence. It was found that in case the handheld consumer device is an electric toothbrush, a period of one second may be a sensible time period for classifying the usage data by means of an ANN, in particular an RNN, and that about 25 temporally equidistant input vectors $x_t$ of usage data may be used. This is of course just one non-limiting example and other values and ranges have already been discussed.

The dimension of the input tuple $x_i$ of an ANN relates to the number of elements of the input data, e.g. if six elements of usage data are used (e.g. six different motion data values from a 3-axis accelerometer and a 3-axis gyroscope), then $x_i \in \mathbb{R}^6$. In case, e.g., a further force value would be added as element to the input usage data, then $x_i \in \mathbb{R}^7$. The output $y_i$ of the ANN depends on the number of usage classes with respect to which the input should be classified. If the number of output classes is e.g. 20, then $y_i \in \mathbb{R}^{20}$. Internally, the size of e.g. the hidden state $h_i$ may have a much larger value. The size of the hidden state $h_i$ may be 256, then $h_i \in \mathbb{R}^{256}$. As will be seen, the input $x_i$ is brought to the higher size by means of a weight matrix W, which is the first example above is $W \in \mathbb{R}^{6 \times 256}$. A bias or threshold b that may be added to the thus size-increased input may have as well the size of the hidden state $h_i$, namely $b \in \mathbb{R}^{256}$. In order to generate the output $y_i$ having a size of 20 from an internal state vector of the ANN having a size of 256, the fully connected output layer uses respective weight matrices $O \in \mathbb{R}^{256 \times 20}$. The numbers used in this paragraph are non-limiting examples and the sizes of the input, the output and of the internal state may have any suitable integer number.

LSTM Unit

Figure 7A:
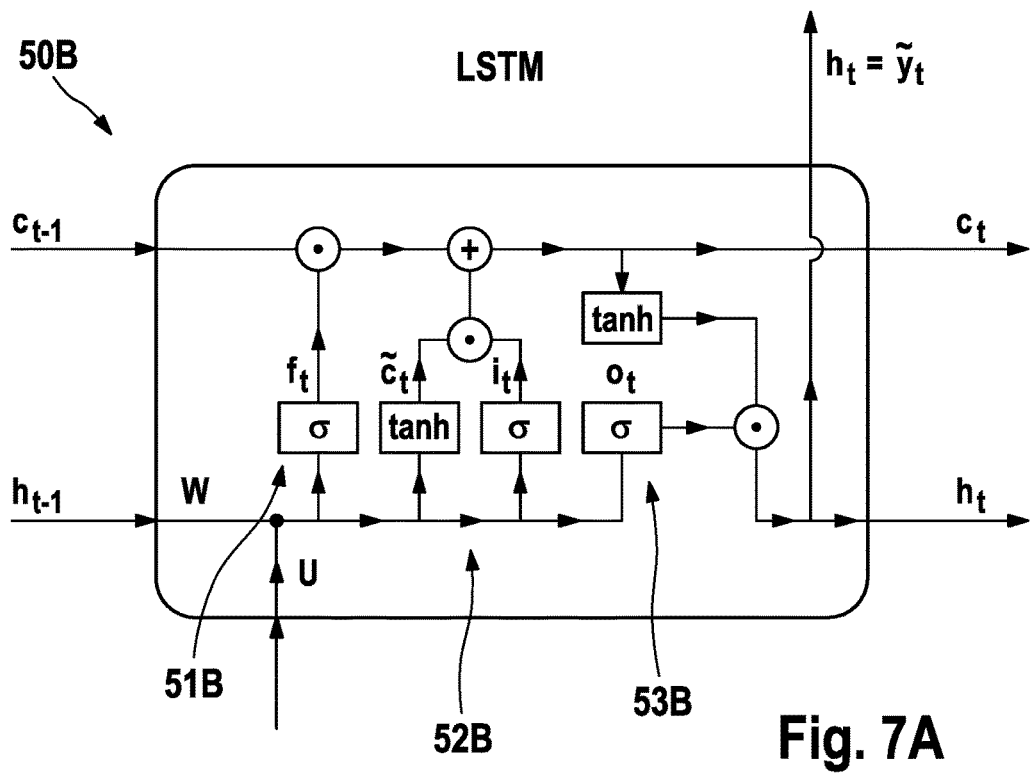
FIG. 7A is a schematic depiction of an example Long Term-Short Memory unit that can be used in a recurrent neural network.

An RNN may be considered as a series of identical feed forward neural network units (one for each time instant) that pass an internal hidden state output as internal hidden state input to the next time instant (the recurrent information) or in other words: a RNN is a single feed forward cell that re-loops the internal hidden state output as new internal hidden state input for each time instant. The RNN unit may have at least one hidden layer. The most basic RNN unit is thus a single layer neural network unit as was already discussed. In a classical "vanilla" RNN unit, the unit's output is identical to the internal hidden state output. The vanilla RNN has known issues (vanishing and exploding gradients, which make the RNN untrainable, and information morphing, which means that the internal hidden state constantly changes in a manner that past information is lost too fast). In 1997, the use of Long Short-Term Memory (LSTM) units was thus proposed to overcome these issues of vanilla RNNs (S. Hochreiter, J. Schmidhuber: Long Short-Term Memory, Neural Computation 9 (8): 1735-1780, 1997). The basic LSTM unit 50B is shown in FIG. 7A. In contrast to the basic RNN unit discussed with reference to FIGS. 6A and 6B, the LSTM unit 50B comprises a hidden state h and a cell state c. The LSTM unit 50B shown in FIG. 7A relates to time instant t. Hence, the LSTM unit 50B receives the cell state $c_{t-1}$ and the hidden state $h_{t-1}$ from the previous time instant and outputs a cell state $c_t$ and a hidden state $h_t$ relating to the present time instant t. The hidden state output $h_t$ is also used as output of the LSTM unit that may be fed forward to the output layer or to another hidden layer, as will be discussed with respect to stacked RNNs further below. In order to solve the issue of a vanilla RNN, the LSTM unit 50B comprises a forget gate 51B, an input gate 52B, and an output gate 53B. All gates 51B, 52B, 53B receive the concatenated vector comprising $h_{t-1}$ and $x_t$ as input. This concatenated input vector goes in each gate through a fully connected layer by means of weight matrices W and U and is then activated by an activation function, where σ stands for the sigmoid function and tan h for the hyperbolic tangent function. Reference is made to the below equations. In FIG. 7A, ⊕ denotes elementwise addition and ⊙ denotes the Hadamard product (i.e. elementwise multiplication). By the forget gate it is decided what portion of the cell state shall be forgotten. By the input gate it is decided what shall be added to the cell state. In the output gate the cell state is used to determine the hidden state output.

The equations relating to this basic LSTM unit are:

$$i_t = \sigma(W_i \cdot h_{t-1} + U_i \cdot x_t + b_i);$$
$$o_t = \sigma(W_o \cdot h_{t-1} + U_o \cdot x_t + b_o);$$
$$f_t = \sigma(W_f \cdot h_{t-1} + U_f \cdot x_t + b_f);$$
$$\tilde{c}_t = \tanh(W_c \cdot h_{t-1} + U_c \cdot x_t + b_c);$$
$$c_t = f_t \odot c_{t-1} + i_t \odot \tilde{c}_t;$$
$$h_t = \hat{y}_t = o_t \odot \tanh(c_t);$$

where $x_t$ is the input vector, $i_t$ is the input gate activation vector, $o_t$ is the output gate activation vector, $f_t$ is the forget gate activation vector, $c_t$ is the cell state vector, $\tilde{c}_t$ is the candidate state vector, and $h_t$ is the hidden state vector that is also the output of the basic LSTM cell. $c_{t-1}$ and $h_{t-1}$ are the hidden state and cell state vectors from the previous time instant. $W_i$, $W_o$, $W_f$, and $W_c$ are the hidden state weight matrices applied before the respective activation function, $U_i$, $U_o$, $U_f$, and $U_c$ are the input weight matrices and $b_i$, $b_o$, $b_f$, and $b_c$ are bias vectors. σ denotes the sigmoid activation function. It shall be noted that herein the terms "tuple" and "vector" are exchangeable.

Various modifications of the basic LSTM unit exist (e.g. LSTM unit with so-called peephole connections). The discussion of the here shown LSTM unit shall be considered as a non-limiting example.

GRU Unit

Another type of RNN can be built by using so-called Gated Recurrent Units (GRUs). GRUs are similar to LSTMs but are to some extent simpler. GRUs were introduced by K. Cho et al. in 2014 ("Learning Phrase Representations using RNN Encoder-Decoder for Statistical Machine Translation", 3 Sep. 2014, arXiv:1406.1078v3).

Figure 7B:
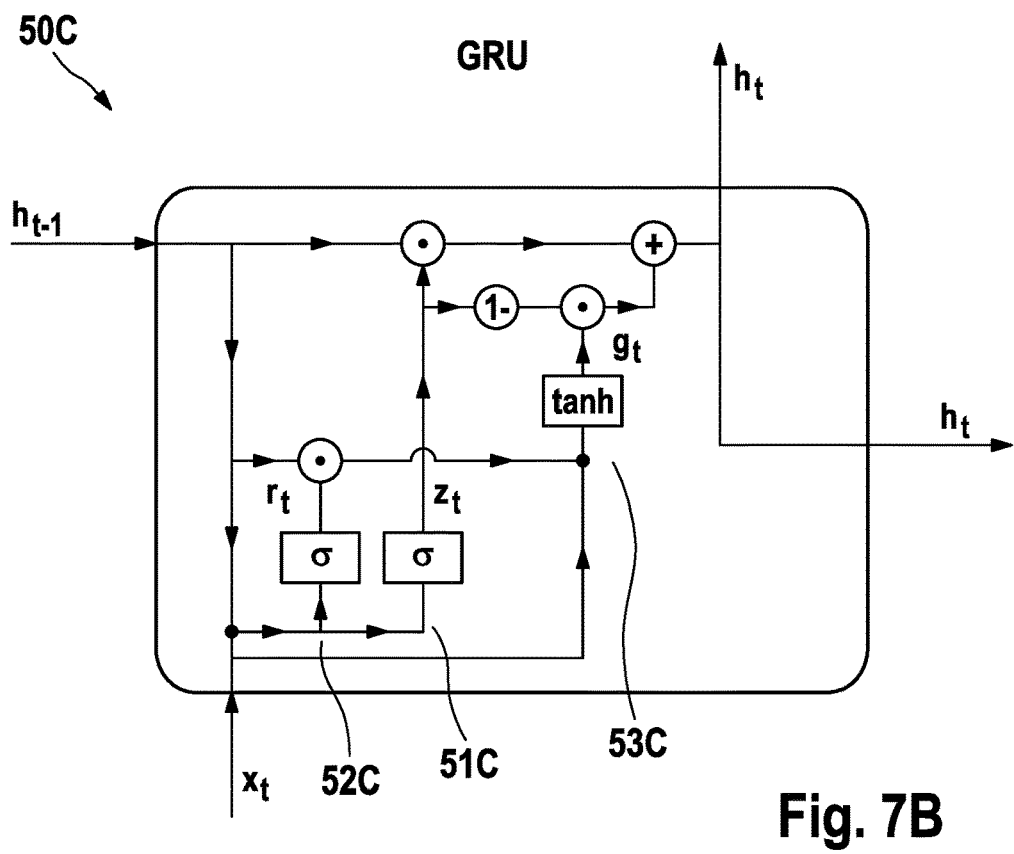
FIG. 7B is a schematic depiction of an example Gated Recurrent Unit that can be used in a recurrent neural network.

A graphical representation of a GRU 50C is shown in FIG. 7B. It can be seen that the GRU 50C does not comprise a cell state as is known from LSTM units. The GRU 50C comprises an update gate 51C, a reset gate 52C, and an output gate 53C.

The equations relating to this basic GRU 50C are:

$$z_t = \sigma(W_z \cdot h_{t-1} + U_z \cdot x_t + b_z);$$
$$r_t = \sigma(W_r \cdot h_{t-1} + U_r \cdot x_t + b_r);$$
$$g_t = \tanh(W_g(r_t \odot h_{t-1}) + U_g \cdot x_t + b_g);$$
$$h_t = \hat{y}_t = z_t \odot h_{t-1} + (1 - z_t) \odot g_t;$$

where $z_t$ is the update gate activation vector, $r_t$ is the reset gate activation vector, $g_t$ is the current memory content and $h_t$ is the final memory at the current time step. There are obvious similarities between the LSTM unit 50B and the GRU unit 50C, but the GRU unit 50C is somewhat less computationally complex. It had been found that a GRU unit based RNN provides similarly high prediction precision as an LSTM unit based RNN and provides this at higher computational speed. In particular for realization on a small processing device such as a smartphone, a GRU unit based RNN may thus be used.

Architectures of RNNs

Figure 8A:
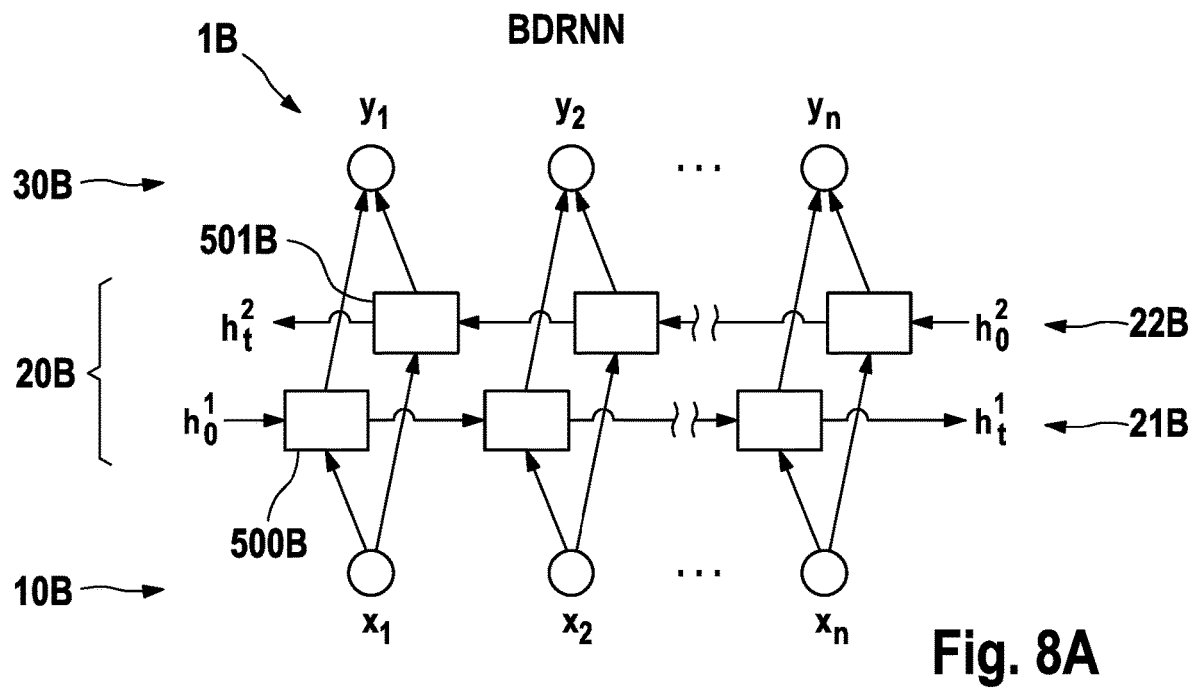
FIG. 8A is a schematic depiction of an example bi-directional recurrent neural network.
Figure 8B:
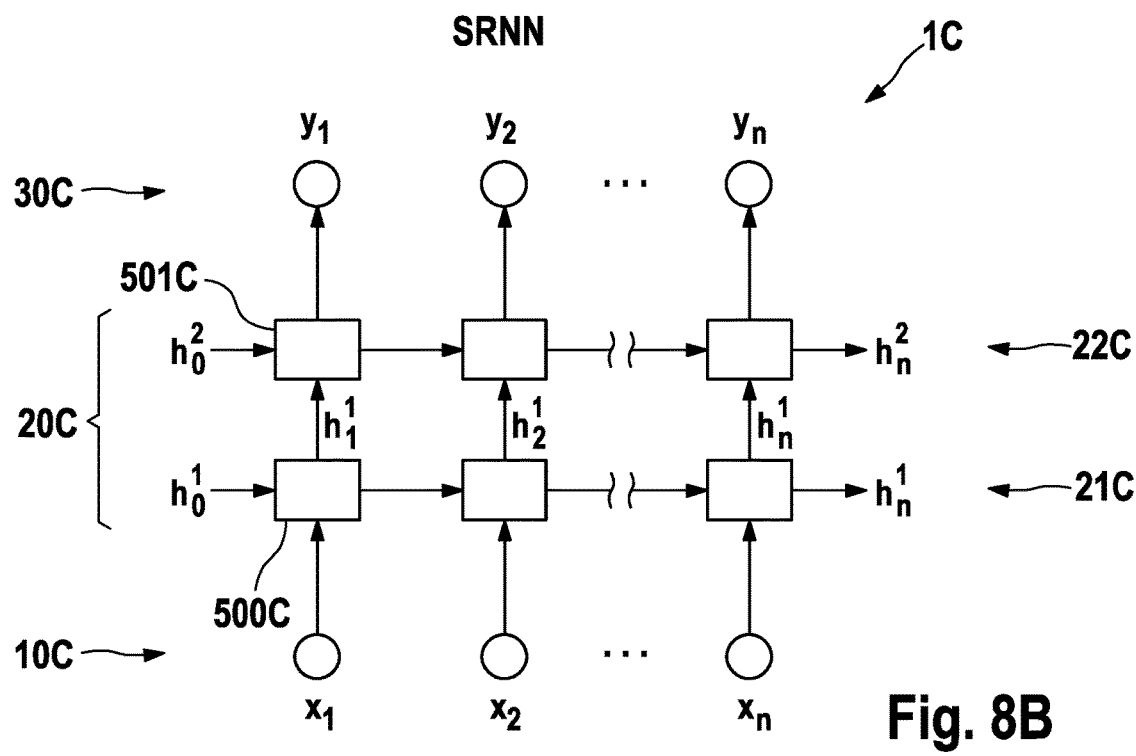
FIG. 8B is a schematic depiction of an example stacked recurrent neural network.
Figure 8C:
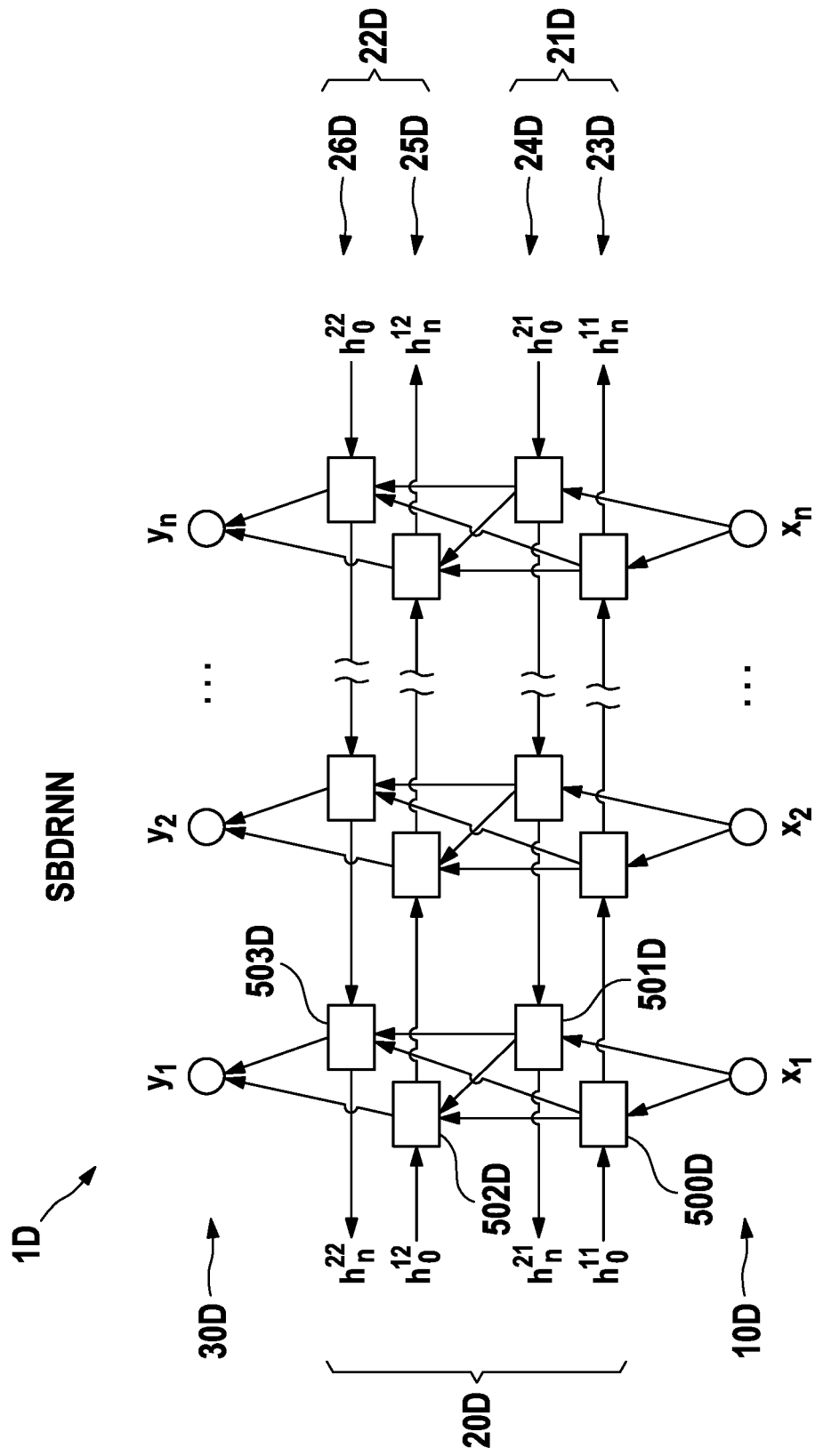
FIG. 8C is a schematic depiction of an example stacked bi-directional recurrent neural network.

A recurrent unit such as units 50A, 50B, or 50C may be used in manifold different architectures of RNNs. Two particular architectures of RNNs are bi-directional RNNs (BDRNN) and stacked RNNs (SRNN). A schematic depiction of a bi-directional RNN is shown in FIG. 8A and a schematic depiction of a stacked RNN is shown in FIG. 8B. For sake of completeness, FIG. 8C shows an example depiction of a stacked bi-directional RNN (SBDRNN).

The BDRNN 1B shown in FIG. 8A computes in parallel from left to right and from right to left the outputs of the RNN units 500B and 501B. The BDRNN 1B comprises an input layer 10B, a hidden layer 20B, and an output layer 30B. The hidden layer 20B comprises a first chain 21B of recurrent units 500B that compute the outputs from left to right (or in a temporal language from past to future) and a second chain 22B of recurrent units 501B by which the outputs are computed from right to left (or in a temporal language from the future to the past). Each of the chains 21B, 22B comprises its own hidden state vector, namely the hidden state vector $h^1$ for the left-to-right chain 21B and the hidden state vector $h^2$ for the right-to-left chain 22B. The outputs of the recurrent units 500B and 501B relating to a given time instant t can be concatenated or element-wise added and are then mapped by a fully connected output layer 30B onto an output vector y for each time instant t. This allows the BDRNN to consider patterns in the input sequence in both time directions.

For the temporally first of the time periods that is assessed by a BDRNN, the hidden state $h_0^1$ (i.e. the hidden state for the forward direction) may be arbitrarily initialized, e.g. each element of $h_0^1$ may be set to 0. The same may be done for $h_0^2$ (i.e. the hidden state for the backward direction). For the temporally next time period that is assessed, $h_0^1$ may be set to $h_n^1$ from the previous assessment. The analyzing device may then be arranged to store the last hidden state in the forward direction for inputting it into the next RNN unit for the assessment of the next sequence of usage data. $h_0^2$ may always be set to have the same initial values if there is no information from the "future". Instead of arbitrarily initializing the hidden states in forward and backward direction, the hidden states can be optimized in the learning phase of the BDRNN, e.g. the initial hidden states may be considered as parameters used by the BDRNN in the learning phase to optimize the prediction. What is said here for the hidden state in forward direction of course also applies for all other RNNs and what is said about the hidden state in the backward direction also applies to a stacked BDRNN described below.

FIG. 8B shows an SRNN 1B that comprises two recurrent units 500C and 501C per time instant t in feed forward direction. Thus, the hidden portion 20C of the SRNN 1B has a first hidden layer 21C and a second hidden layer 22C that are coupled in feed forward direction. The hidden state vector $h_1^1$ that is forwarded from recurrent unit 500C of the first hidden layer 21C to the next time instant is also fed forward as input vector to recurrent unit 501C of the second hidden layer 22C. The SRNN IC definitely may be considered a deep neural network. Where a single hidden layer LSTM unit or GRU may be considered a deep neural network because of the four or three layers, respectively, in each LSTM unit or GRU, a stacked LSTM or stacked GRU network adds even further depth.

FIG. 8C shows a schematic depiction of a SBDRNN 1D, which combines the structures of a BDRNN as shown in FIG. 8A and of a SRNN as shown in FIG. 8B. The hidden portion 20D of the SBDRNN 1D thus has two stacked hidden layers 21D and 22D. The hidden layers 21D, 22D each comprise a left-to-right layer 23D and 25D, respectively, and a right-to-left layer 24D and 26D, respectively. This offers the opportunity that the output of the recurrent units 500D and 501D of the first hidden layer 21D is fed forward to each of the recurrent units 502D and 503D of the second hidden layer 22D (e.g. the outputs are concatenated and are then fed into the respective recurrent unit 502D and 503D). It had been found that a stacked bi-directional LSTM or GRU provides a good prediction quality for the classification tasks discussed herein. It was also found that the internal dimension of such a LSTM or GRU network does not need to go beyond about 256 (where "dimension" here refers to the hidden state vectors, which means that the hidden states are 256-tuples), which allows on the one hand for live prediction results of the ANN when implemented on a smartphone or tablet computer etc., in particular when combined with a sequence length of about 25 samples and on the other hand provides sufficient prediction quality. This shall not be considered as limiting and hidden state vector dimensions in the range of, e.g., between 128 to 512 (or numbers around these values) and sequence lengths in the range of, e.g., between 10 to 50 (or around thee values) are also considered.

Output of the ANN and Successive Operations on the Output

In the various example RNNs 1A, 1B, 1C, and 1D discussed herein, an output vector or tuple $y_t$ is generated for every time instant. This shall not be considered as limiting. But for the discussion of the present chapter it shall be assumed that for each input sequence $x=(x_1, x_2, \ldots, x_n)$ at least two outputs are provided by the RNN. For sake of simplicity, the output sequence $y=(y_1, y_2, \ldots, y_n)$ of the RNN is here considered to have the same length as the input sequence. Further and without being limited by theory, the ANN may apply a softmax function onto each output tuple $y_i$. The softmax function normalizes the elements of the output $y_i$ so that the elements of the output vector $y_i$ sum up to 1 and are squeezed into the range of [0, 1]. But this is considered an optional step. Each input vector $x_i$ of the input sequence may be a tuple having dimension k, e.g. k=6 if six inertial sensor data values are used or k=7 if an additional force sensor value or another sensor value is used. Each output vector $y_i$ may be a tuple having dimension m, e.g. m=20. As was already discussed, the elements of the output $y_i$, i.e. $y_i=(y_i(1), y_i(2), \ldots, y_i(m))$ relate to the different usage classes of the set of usage classes used by the ANN.

For a handheld consumer device, each element of the output vector $y_i$ at a given time instant relates to a prediction that the input belongs to the usage class to which this element is assigned. In an example where the input vectors $x_i$ only comprise motion data, and the consumer device is an electric toothbrush, the usage classes may thus be different motion types, e.g. the first usage class may relate to a motion of slow brusher and the second usage class may relate to a motion of a fast brusher. In accordance with the main task of the present disclosure, namely to provide a determination (i.e. prediction with sufficiently high probability) of the location of the consumer device, each element of an output vector $y_i$ may thus relate to the motion typical for usage of the consumer device in one or several zones of the target surface. E.g. the first element of the output $y_i$, namely $y_i(1)$, may relate to motion typical for the buccal surfaces of the upper left molars and the second element $y_i(2)$ may relate to a motion typical for the occlusal surfaces of the upper left molars. In case that the relevant zone for communication to the consumer is "upper left molars", then the first and the second element of the output are associated with this zone. Further assume that elements three and four of the output relate to motions typical for the buccal and occlusal surfaces of the lower left molars, respectively, which both are associated with the zone "lower left molars" and that the fifth element relates to motions typical for brushing the buccal surfaces of the upper and lower molars together (consumers may brush these buccal surface in a single go by keeping the jaws closed). Then the fifth element of the output is associated with the zones "upper left molars" and "lower left molars". This example shows that several elements of the output vector $y_i$ may be associated with one portion of the target space and that also one given element of the output vector $y_i$ may be associated with two or more portions of the target surface. While this example was given with respect to motions typical for certain portions of a target space, it shall be understood that the same is true for all other associations between usage classes of the ANN and output vectors as well. While this example has shown a rather complex association matrix between the classes of the ANN and the portions of the target space, it shall be understood that a simple one-on-one and onto relationship (i.e. a bijective relationship) between usage classes of the ANN and portions of the target space also falls within the gist and scope of the present disclosure. In this latter case, a differentiation between the usage classes and the portions of the target space is of course of academic nature.

The system may in particular be arranged to provide a single usage class answer only for a predetermined number of output tuples, e.g. the system may provide a single usage class answer only per input sequence. In order to provide the single usage class answer, an argmax function may be applied to each output tuple so that the number of the tuple element having the highest value is selected. By applying the argmax function, a threshold may be applied so that those elements that have the highest value but lie below a threshold will not be selected. For an output tuple on which the softmax function was applied, the threshold may be chosen to lie in the range of between 0.5 and 0.99, in particular in the range of between 0.6 and 0.9, further in particular in the range of between 0.65 and 0.8, for example where the threshold is set to 0.7. After the argmax function is used to select a usage class for a single time instant, a maximum criterion or majority criterion may be used to select one usage class as the single usage class answer for the entire input sequence.

Systems with One ANN Used for Two Successive Tasks

It has been described that an ANN can be used to classify the usage of a consumer device based on usage data. The classification may in particular happen live, i.e. during a usage session.

In some cases, it may be wishful to identify the current user, e.g. to store the results of the classification and other data from the current usage session in the user's account so that the user can later access his or her own data. User identification may happen by using at least a portion of the temporal sequence of the classification output of the system for the current usage session and to compare with stored usage data from the different users of the consumer device. By applying, e.g., a similarity check (e.g. distance computation) of the current at least portion of the classification output with a stored respective portion of a classification output (e.g. the first 10 seconds of the usage), the user may be identified. That means while the ANN generates classification output that is communicated to the user, the system can in parallel also identify the user by using the same classification output. Instead of using usage data to identify the user, the individual user may be determined by analyzing the single usage class answers provided during at least a portion of the usage session. Each user may have his or her own "fingerprint" that can be identified.

Systems with Two or More ANNs

In some embodiments, the system described herein may comprise two different ANNs. Two ANNs shall be different if they have either two different architectures or two different sets of weights and biases. Without introducing any limitations, the latter case is discussed to exemplify the respective system.

As was said, on a global level the users of a consumer device show various different usage characteristics, which characteristics may be grouped. In a simple example, users of a consumer device may be grouped into fast users and into slow users, where here fast and slow may relate to the way in which the consumer device is moved. E.g. in case of an electric toothbrush, a slow user may stick to one tooth for a certain time until the tooth is sufficiently brushed and would then go to the neighboring tooth etc. In contrast, a fast user may jump between teeth with a high frequency. An ANN as described above is typically trained with labelled input from both types of users. The prediction should thus cover both groups of users. But it can be contemplated that an ANN may provide a higher prediction probability in case usage data from a fast user is fed into an ANN that was trained with only usage data from fast users and usage data from a slow user is fed into an ANN that was trained with only usage data from slow users. Hence, a system is considered where the usage data of a user is first fed into a classification unit (which may be ANN-based, but which may also use a statistical classification algorithm or any other machine learning-based classification algorithm) by which it is classified whether the user is a fast or a slow user, i.e. the target space comprises two portions, one that relates to fast users and one that relates to slow users. Or in other words, the classification unit (e.g. a first ANN) classifies the usage data with respect to two usage classes, namely fast users and slow users. Once the type of user has been identified (which may only take a few seconds and may thus be done just at the beginning of a usage session), the usage data is fed into a second ANN that comprises weights and biases that are specific for the respective user type (i.e. the second ANN being chosen from a group comprising at least two specific ANNs). Such a scenario may be easily extended, e.g. by adding a third user group, which may be medium users, i.e. users that are neither particularly slow nor particularly fast. After the first classification unit (e.g. first ANN) has done the respective classification of the user group, the second ANN may then be chosen from a group of three ANNs that each may have the same architecture but have different weights and biases due to the different learning input. As an alternative, the usage data may be input into two or more ANNs in parallel, each ANN being specifically trained for, e.g., one particular user group, and the selection of the appropriate ANN happens later, e.g. simply by choosing the ANN that provides the highest prediction values during a sample time or during the complete usage session or after having done a "fingerprint" analysis (see previous chapter).

In other examples, a system has two different ANNs that are used. Using again an example from the area of electric toothbrushes, a first ANN is used to classify the received usage data with respect to motion relating to brushing the upper jaw or the lower ja and a second ANN may be used in parallel to classify the very same usage data with respect to motions relating to brushing the left molars, the right molars or the front teeth. By a combination of the output of the two ANNs a portion of the target space can be identified that may have a higher prediction probability in contrast to using a single ANN that classifies the motion with respect to motions relating to brushing the upper left molars, the upper right molars, the upper front teeth, the lower left molars, the lower right molars, and the lower front teeth.

In other examples building on the previous exemplifications, three ANNs are used that each classify one individual aspect of the usage of the consumer device (where here individual aspects means that the different ANNs classify the usage of the consumer device with respect to a different set of usage classes). As one example: the first ANN classifies the usage data with respect to upper and lower jaw, the second ANN classifies usage data with respect to left molars, right molars and front teeth, and the third ANN classifies usage data with respect to buccal, lingual, and occlusal surfaces for the molars and front and back surfaces of the front teeth. As was stated before, due to the limited number of motion classes per NN, the prediction quality for each of the ANNs may be higher and thus means that the combination of the results of the three ANNs (e.g. current brushing motion was classified as (1) upper jaw, (2) left molars, and (3) occlusal surfaces) may be more precise then the classification by a single ANN by which this level of differentiation shall be achieved.

Systems with Different ANNs Used for the Same Task

In some embodiments, two or more different ANNs are used to classify the input with respect to the same set of usage classes. While there are several possibilities to handle the outcome of different ANNs that have the same task, the outputs from the different ANNs may in some examples be combined by summing or averaging the elements of the output tuples before the element having the highest prediction value is identified (e.g. by applying the argmax function). As was discussed before, thresholds may be defined in this process so that a final prediction value below a certain threshold may be discarded. Also in case of two different ANNs, the outcome may be discarded (e.g. will not be communicated to the user) if the two ANNs provide two different usage classes that each have a certain prediction value above a certain threshold value.

Deep learning frameworks such as TensorFlow, Microsoft Cognitive Toolkit, PyTorch, Caffe, or Theano may be used to build an RNN like an LSTM or a GRU RNN. Open source libraries such as Keras may be used to run on top of such frameworks, i.e. to provide an interface to these frameworks.

TensorflowLite, CoreML, TensorRT or customized libraries may also be used to productize deep models on smartphones, other edge computing devices or cloud computing devices.

It shall be noted that while the present disclosure focused on RNNs of certain structures (e.g. LSTM and GRU), this shall not mean that this shall be considered as limiting and in particular other RNN architectures may be used as well, e.g. clockwork RNNs and other multi-timescale RNNs such as phased LSTMs or hierarchical RNNs or, as another example, dilated RNNs may be used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for classifying the usage of a consumer appliance, the system comprising:
    the consumer appliance comprising a sensor unit including at least one of an inertial sensor, a gyroscope, a magnetometer, and a force sensor, the sensor unit being structured to determine at least one usage data at successive time instants and to provide a temporally successive sequence of usage data relating to a motion of the consumer appliance or a force acting thereon during a usage session; and
    an analyzing device comprising a processor and structured to classify the usage of the consumer appliance with respect to at least one set of at least two usage classes relating to different usage properties, wherein the analyzing device assembles a temporally successive sequence of input tuples of usage data relating to a predetermined time period of the usage session, each of the input tuples comprising at least one element representing the usage data at the respective time instant and for inputting the sequence of input tuples into at least one artificial neural network that is arranged to output at least one output tuple that comprises a number of elements in accordance with the number of usage classes, each element of the output tuple representing a prediction value that the usage of the consumer appliance at the given time instant relates to a respective usage class, and wherein the analyzing device determines a single usage class answer for the time period based on the sequence of output tuples.

2. The system of claim 1, wherein the consumer appliance and the analyzing device are physically separate from each other and are structured to be coupled for wireless communication, wherein the consumer appliance samples raw usage data at a first frequency and transmits processed raw usage data as the usage data to the analyzing device at a second frequency that is equal to or lower than the first frequency.

3. The system of claim 2, wherein the consumer appliance is structured to reduce the resolution of the usage data prior to transmission, wherein the usage data have a resolution of about 10 bit or below.

4. The system of claim 1, the first frequency is about 100 Hz or higher, and the second frequency is about 100 Hz or lower.

5. The system of claim 1, wherein the at least one artificial neural network is a recurrent neural network selected from the group consisting of a bi-directional LSTM or GRU network, a stacked LSTM or GRU network, and a stacked bi-directional LSTM or GRU network.

6. The system of claim 1, wherein the analyzing device, in operation, uses at least two different artificial neural networks to classify the usage of the consumer appliance, wherein the analyzing device performs at least one of the following procedures:
    using a first of the at least two different artificial neural networks to determine a second of the at least two different artificial neural networks for classifying the usage of the consumer appliance;
    using the at least two different artificial neural networks in parallel for classifying the usage of the consumer appliance with respect to the same set of usage classes; and
    using the at least two different artificial neural networks in parallel for classifying the usage of the consumer appliance with respect to different sets of usage classes.

7. The system of claim 1, wherein the sensor unit comprises at least one further sensor selected from the group consisting of a pH sensor, a temperature sensor, a capacitive sensor, an audio sensor, a light sensor, a picture sensor, a video sensor, a barometric sensor, and any combination thereof, wherein the sensor unit, in operation, provides a temporally successive sequence of sensor data of the at least one further sensor during the treatment period, and wherein the usage data comprises the at least one further sensor data and each of the input tuples comprises at least one element representing the at least one further sensor data at the respective time instant.

8. The system of claim 1, wherein the predetermined time period is from 0.1 seconds to 5 seconds.

9. The system of claim 8, wherein the predetermined time period is from 0.25 seconds to 2 seconds.

10. The system of claim 8, wherein the number of temporally successive input tuples of usage data within the predetermined time period is from 5 to 100.

11. The system of claim 10, wherein the number of temporally successive input tuples of usage data within the predetermined time period is from 10 to 50.

12. The system of claim 1, wherein a size of the hidden state in the artificial neural network is about 256 or lower.

13. The system of claim 1, wherein the analyzing device is structured to utilize a maximum criterion or a majority criterion in the determination of the single usage class answer.

14. The system of claim 1, wherein the analyzing device is structured to discard an output tuple element in the determination the unique usage answer single usage class answer that has a normalized value below a threshold value, wherein the threshold value is from 0.5 and 0.99.

15. The system of claim 14, wherein the threshold value is from 0.6 to 0.9.

16. The system of claim 15, wherein the threshold value is from 0.65 to 0.8.

17. The system of claim 1, wherein the different usage properties are selected from the group consisting of at least two different motion patterns, at least two different users or types of users, at least two different motion qualities, at least two different portions of a target space, and any combination thereof.

18. The system of claim 17, wherein the different usage properties relate to the at least two different motion qualities selected from the group consisting of good usage, bad usage, correct usage, incorrect usage, and any combination thereof.

19. The system of claim 1, wherein the consumer appliance is arranged to store the usage data of at least one usage session and to transmit the usage data only after the end of the usage session or after a plurality of usage sessions.

20. The system of claim 19, wherein the consumer appliance is arranged to store the usage data of at least one usage session and to transmit the usage data only after transmission of the usage data is requested by a user or the analyzing device.

21. The system of claim 1, further comprising a user-feedback unit selected from the group consisting of a display, a plurality of light emission elements, a drive unit of the consumer appliance, an audio feedback unit, and any combination thereof, for communicating information related to the classification.

22. The system of claim 1, wherein the sensor unit comprises at least one inertial sensor and at least one force sensor and wherein the usage data comprises at least seven elements of which at least six elements relate to a motion of the consumer appliance and at least one element relates to a force applied at the consumer appliance.

* * * * *